(12) United States Patent
Liu et al.

(10) Patent No.: US 7,402,835 B2
(45) Date of Patent: Jul. 22, 2008

(54) HETEROATOM-CONTAINING DIAMONDOID TRANSISTORS

(75) Inventors: Shenggao Liu, Hercules, CA (US);
Jeremy E. Dahl, Palo Alto, CA (US);
Robert M. Carlson, Petaluma, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 557 days.

(21) Appl. No.: 10/622,046

(22) Filed: Jul. 16, 2003

(65) Prior Publication Data

US 2004/0021204 A1 Feb. 5, 2004

Related U.S. Application Data

(60) Provisional application No. 60/397,483, filed on Jul. 18, 2002.

(51) Int. Cl.
*H01L 51/00* (2006.01)
(52) U.S. Cl. .................. 257/40; 257/E51.001
(58) Field of Classification Search .................. 257/77, 257/40; 544/106
See application file for complete search history.

(56) References Cited

U.S. PATENT DOCUMENTS

| | | | |
|---|---|---|---|
| 3,457,318 A | 7/1969 | Capaldi et al. | |
| 3,832,332 A | 8/1974 | Thompson | |
| 4,225,734 A | 9/1980 | McMurry | |
| 5,017,734 A | 5/1991 | Baum et al. | |
| 5,019,660 A * | 5/1991 | Chapman et al. | 585/22 |
| 5,051,785 A | 9/1991 | Beetz, Jr. et al. | |
| 5,057,894 A * | 10/1991 | Ikeda et al. | 257/370 |
| 5,072,264 A | 12/1991 | Jones | |
| 5,075,757 A | 12/1991 | Ishii et al. | |
| 5,099,296 A | 3/1992 | Mort et al. | |
| 5,107,315 A | 4/1992 | Kumagai et al. | |
| 5,112,775 A | 5/1992 | Iida et al. | |
| 5,117,267 A | 5/1992 | Kimoto et al. | |
| 5,132,749 A | 7/1992 | Nishibayashi et al. | |
| 5,144,380 A | 9/1992 | Kimoto et al. | |
| 5,171,632 A | 12/1992 | Heeger et al. | |

(Continued)

FOREIGN PATENT DOCUMENTS

DE    2545292    4/1979

(Continued)

OTHER PUBLICATIONS

International Search Report from PCT/US03/22630 dated Aug. 20, 2004.

(Continued)

*Primary Examiner*—Richard T. Elms
*Assistant Examiner*—Michael Lulis
(74) *Attorney, Agent, or Firm*—Crowell & Moring LLP

(57) ABSTRACT

These heterodiamondoids are diamondoids that include heteroatoms in the diamond lattice structure. The heteroatoms may be either electron donating, such that an n-type heterodiamondoid is created, or electron withdrawing, such that a p-type heterodiamondoid is made. Bulk materials may be fabricated from these heterodiamondoids, and the techniques involved include chemical vapor deposition, polymerization, and crystal aggregation. Junctions may be made from the p-type and n-type heterodiamondoid based materials, and microelectronic devices may be made that utilize these junctions. The devices include diodes, bipolar junction transistors, and field effect transistors.

38 Claims, 19 Drawing Sheets

U.S. PATENT DOCUMENTS

| | | | |
|---|---|---|---|
| 5,177,585 | A | 1/1993 | Welbourn |
| 5,210,431 | A | 5/1993 | Kimoto et al. |
| 5,223,721 | A | 6/1993 | Iida et al. |
| 5,278,431 | A | 1/1994 | Das |
| H1287 | H | 2/1994 | Zeisse et al. |
| 5,294,814 | A | 3/1994 | Das |
| 5,306,928 | A | 4/1994 | Kimoto et al. |
| 5,331,183 | A | 7/1994 | Sariciftci et al. |
| 5,352,908 | A | 10/1994 | Kobashi et al. |
| 5,371,378 | A | 12/1994 | Das |
| 5,371,382 | A | 12/1994 | Venkatesan et al. |
| 5,382,684 | A | 1/1995 | Moini et al. |
| 5,382,809 | A | 1/1995 | Nishibayashi et al. |
| 5,389,799 | A | 2/1995 | Uemoto |
| 5,400,427 | A * | 3/1995 | Ashjian et al. ............... 385/102 |
| 5,414,189 | A | 5/1995 | Chen et al. |
| 5,449,531 | A | 9/1995 | Zhu et al. |
| 5,454,880 | A | 10/1995 | Sariciftci et al. |
| 5,455,432 | A | 10/1995 | Hartsell et al. |
| 5,470,505 | A | 11/1995 | Smith et al. |
| 5,476,812 | A | 12/1995 | Kimoto et al. |
| 5,478,650 | A | 12/1995 | Davanloo et al. |
| 5,531,184 | A | 7/1996 | Muranaka et al. |
| 5,541,423 | A | 7/1996 | Hirabayashi |
| 5,600,156 | A | 2/1997 | Nishibayashi et al. |
| 5,632,812 | A | 5/1997 | Hirabayashi |
| 5,653,800 | A | 8/1997 | Kucherov et al. |
| 5,656,828 | A | 8/1997 | Zachai et al. |
| 5,747,118 | A | 5/1998 | Bunshah et al. |
| 5,792,256 | A | 8/1998 | Kucherov et al. |
| 5,903,015 | A | 5/1999 | Shiomi et al. |
| 6,110,276 | A | 8/2000 | Yu et al. |
| 6,162,412 | A | 12/2000 | Fujimori et al. |
| 6,235,851 | B1 | 5/2001 | Ishii et al. |
| 6,274,837 | B1 | 8/2001 | Windischmann et al. |
| 6,335,245 | B2 | 1/2002 | Park et al. |
| 6,340,393 | B1 | 1/2002 | Yoshida |
| 6,352,884 | B1 | 3/2002 | Yu et al. |
| 6,376,276 | B1 | 4/2002 | Oishi et al. |
| 6,861,569 | B2 | 3/2005 | Dahl et al. |
| 2002/0016414 | A1* | 2/2002 | Lau et al. .................... 525/132 |
| 2004/0059145 | A1 | 3/2004 | Liu et al. |

FOREIGN PATENT DOCUMENTS

| | | |
|---|---|---|
| EP | 0272418 A2 | 6/1988 |
| EP | 0286306 A1 | 10/1988 |
| EP | 1071141 A2 | 1/2001 |
| EP | 1088875 A2 | 4/2001 |
| JP | 2001026541 | 1/2001 |
| JP | 2001026591 | 1/2001 |
| WO | WO 88/02792 * | 4/1988 |
| WO | WO 92/13909 A1 | 8/1992 |
| WO | WO 95/06019 A1 | 3/1995 |
| WO | WO 02/00505 | 1/2002 |
| WO | WO02/057201 A2 | 7/2002 |
| WO | WO 02/058139 A2 | 7/2002 |
| WO | 03/050066 A1 | 6/2003 |
| WO | WO03/005066 A1 | 6/2003 |
| WO | WO 2004/009577 A1 | 1/2004 |

OTHER PUBLICATIONS

Das, K.K., "Electronic Applications of Diamond Films and Coatings" from *Diamond Films and Coatings*, pp. 381-410, Noyes Publications, R.F. Davis, editor, Park Ridge New Jersey (1993).

Partial ISR from PCT/US03/22630 mailed May 28, 2004.

U.S. Appl. No. 10/046,486, filed Jan. 16, 2002.

Askeland, D.R., "Electrical Conductivity", Chapter 17, pp. 664-667, *The Science and Engineering of Materials Second Edition*, J. Donald Childress ed. (1989).

Balaban et al., Systematic Classification and Nomenclature of Diamond Hydrocarbons -I, *Tetrahedron* 34:3599-3606 (1978).

Baugman, G.I., "Dibromination of Adamantane", (1964).

Becker et al, "A Short Synthese of 1-azaadamantan-4-one and the 4r and 4s Isomers of 4-Amino-1-azaadamantane", *Synthesis* 11:1080-1802 (1992).

Bingham, R.C. et al., Chapter 18 of "Chemistry of Adamantanes", *Springer-Verlag* (1971).

Bishop, R., et al., "Detection of Non-Conjugative Interactions in Rigid Cyclic Molecules by Using Carbon-13 N.M.R. Shift Values", *Aust. J. Chem.* 40:249-255 (1987).

Black, R.M. et al., "Adamantane Chemistry. Part 3. Abnormal Hypoiodite Reactions of 2-Substituted Adamantan-2-ols; Synthetic Routes to 4-Oxahomo-and 2-Oxa-adamantanes, and 7-Substituted-bicyclo[3.3.1]nona-3-ols", *J. Chem. Soc. Perkins Trans.* I 410-418 (1980).

Blaney et al, "Chemistry of Diamantane, Part II. Synthesis of 3,5-disubstituted Derivatives", *Synthetic Communications* 3(6):435-439 (1973).

Boudjouk et al, "Synthesis and Reactivity of 1-Silaadamantyl Systems", *Journal of Organometallic Chemistry* 2:336-343 (1983).

Boudjouk et al, "The Reaction of Magnesium with cis-1,3,5-Trsi(bromomethyl)cyclohexane. Evidence For a Soluble Trigrignard", *Journal of Organometallic Chemistry* 281:C21-C23 (1985).

Bubnov et al, "A Novel Method of Synthesis of 1-azaadamantane from 1-boraadamantane", *Journal of Organometallic Chemistry* 412:1-8 (1991).

Cao, G.Z., "Nitrogen and Phosphorus Doping in CVD Diamond", *Diamond*, edited by M.H. Nazare and A.J. Neves, INSPEC pp. 345-347 (2001).

Chakrabarti et al., "Chemistry of Adamantane. Part II. Synthesis of 1-Adamantyloxyalkylamines", *Tetrahedron Letters* 60:6249-6252 (1968).

"Computation Concepts" *Chem3D Molecular Modeling and Analysis User's Guide*, Chapter 9, pp. 123-144.

Courtney, T., Johnston, D.E. McKervey, M.A. and Rooney, J.J., "The Chemistry of Diamantanes. Part 1. synthesis and Some Functionalisation Reactions", *J. Chem. Soc. Perkin I* 2691-2696 (1972).

Das, K.K., "Electronic Applications of Diamond Films and Coatings", from Diamond Films and Coatings: Development, Properties, and Applications, Robert F. Davis, Ed., *Noyes Publications*, pp. 381-410 (1993).

DeFranceschi, S., et al., "Electronics and the Single Atom", *Nature* 417:701-702 (2002).

Eguchi et al, "A Novel Route to the 2-Aza-adamantyl System via Photochemical Ring Contraction of Epoxy 4-Azahomoadamantanes", *Journal of Organometallic Chemistry, Commun.*, 1147-1148 (1984).

Fernandez, M.J., et al., "NMR Study of 1-Azatricyclo[3.3.1$^{3-7}$]decane Derivatives", *J. Heterocyclic Chem.* 26:307-312 (1989).

Fernandez, M.J., et al., "Synthesis, Structural and Conformational Study of 4-α-(or β)-*p*-Chlorobenzoyloxy-1-azaadamantane Hydrochloride", *J. Heterocyclic Chem.* 26:349-353 (1989).

Fleming, I., et al., "A New Oxindole Synthesis", *J. Chem. Soc. Perkin Trans.* 1:617-626 (1991).

Fort, Jr., et al., "Stereochemistry of Hydride Reductions of 4,8-Dihalo-2-thiaadamantanes and Related Thiabicyclo[3.3.1]nonanes", *J. Org. Chem.* 52:2396-2399 (1987).

Fox, M.A., et al., "Transmission of Electronic Effects by Icosahedral Carboranes; Skeletal Carbon-13 Cehmical Shifts and Ultraviolet-Visible Spectra of Substituted aryl-*p*-carboranes (1,12-dicarba-*closo*-dodecaboranes)", *J. Chem. Soc., Dalton Trans.* 401-411 (1998).

Fritz, G., et al., "Silicon-Carbon Compound with a Carborundum Structure", Abstract, *Angew, Chem, Internat. Edit.* 9(6) (1970).

Fritz, G., et al., "Uber die Isolierung Hoherer Carbosilane aus der Pyrolyse des Tetramethylsilans", *Z. anorg. allg. Chem.* 512 pp. 103-125 (1984).

Gagneux et al, "1-Substituted 2-heteroadamantanes", *Tetrahedron Letters* 17: 1365-1368 (1969).

Galasso, V., "A Green's Function ab Initio Study of the Outer Valence Ionization Potentials of Adamantane and Hereto Derivatives", *Journal of Molecular Structure (Theochem)* 336:47-54 (1995).

Gerzon, et al., "The Adamantyl Group in Medicinal Agents, 1. Hypoglycemic N-Arylsulfonyl-N-adamantylureas", *Journal of Medicinal Chemistry* 6:(6):760-763 (1963).

Hass, et al., Adamantyoxycarbonyl, a New Blocking Group. Preparation of 1-Adamantyl Chloroformate, *Journal of the American Chemical Society* 88(9):1988-1992 (1966).

Hahn, J.M. et al., "Strongly Enhanced Stereoselectivity in the Reduction of of 5-Substituted Adamantanones by Substitution of $C_5$ by Positive Nitrogen", *J. Am. Chem. Soc.* 114:1916-1917 (1992).

Hawley, "Condensed Chemical Dictionary", 14th ed., John Wiley & Sons, Inc., 2001.

Henkel et al, "Neighboring Group Effects in the β-halo Amines. Synthesis and Solvolytic Reactivity of the anti-4-Substituted 2-Azaadamantyl System", *Journal of Organometallic Chemistry* 46:4953-4959 (1981).

Jackman, R.B., "Diamond Optoelectronic Devices", edited by M.H. Nazare and A.J. Neves, INSPEC pp. 393-398 (2001).

Jawdosiuk, M., et al., "Photolysis and Thermolysis of 3-Azidonoradamantane. "Anti-Bredt" Imines, 2-asa-adamant-1-ene, and 4-Azaprotoadamant-3-ene", *J. Chem. Soc. Perkin Trans* 1:2583-2585 (1984).

Johnston, C., et al., "Boron Doping and Characterisation of Diamond", *Diamond*, edited by M.H. Nazare and A.J. Neves, INSPEC pp. 337-344 (2001).

Jones, R., et al., "Theory of Aggregation of Nitrogen in Diamond", edited by M.H. Nazare and A.J. Neves, INSPEC pp. 127-129 (2001).

Kalish, R., et al., "Doping of Diamond Using Ion Implantation", *Diamond*, edited by M.H. Nazare and A.J. Neves, INSPEC pp. 321-330 (2001).

Kiflawi, I., et al, "Aggregates of Nitrogen in Diamond", edited by M.H. Nazare and A.J. Neves, INSPEC pp. 130-133 (2001).

Kiflawi, I., et al, "The Nitrogen Interstitial in Diamond", edited by M.H. Nazare and A.J. Neves, INSPEC pp. 134-135 (2001).

Krasutsky, P.A., et al., "A New One-Step Method for Oxaadamantane Synthesis", *Tetrahedron Letters* 37(32):5673-5674 (1996).

Krasutsky, P.A., et al., "Observation of a Stable Carbocation in a Consecutive Criegee Rearrangement with Trifluoroperacetic Acid", *J. Org. Chem.* 65:3926-3933 (2000).

Krishnamurthy et al, "Heteroadamantanes. 2. Synthesis of 3-Heterodiamantanes", *Journal of Organometallic Chemistry*, 46(7):1389-1390 (1981).

Kroschwitz, J.I., ed, "Electrically Conductive Polymers" pp. 174-219 from *High Performance Polymers and Composites, John Wiley & Sons* (1991).

Kurtsiefer, C., et al., "Stable Solid-State Source of single Photons", *Physical Review Letters* 85(2):290-293 (2000).

Lansbury, et al., "Some Reactions of α-Metalated Ethers", *The Journal of Organic Chemistry* 27(6):1933-1939 (1962).

Lawson, S.C., et al., "The effect of Transition Metals (TM) on the Aggregation Kinetics of Nitrogen in Diamond", edited by M.H. Nazare and A.J. Neves, INSPEC pp. 172-173 (2001).

Liaw, D.J, et al., "Synthesis and Characterization of New Polyamides and Polyimides Prepared from 2,2-bis[4-(4-aminophenoxy)phenyl]adamantane", *Macromol. Chem. Phys.* 200(6):1326-1332 (1999).

Lin, et al., "Natural Occurrence of Tetramantane ($C_{22}H_{28}$), Pentamantane ($C_{26}H_{32}$) and Hexamantane ($C_{30}H_{36}$) in a Deep Petroleum Reservoir", *Fuel* 74(10):1512-1521 (1995).

Lippert, E., et al., "Darstellung and UV-Spektren einiger Fluorenon-Derivate", *Angew. Chem.* 71:429-430 (1959).

Makarova, et al., "Psychotropic Activity of Some Aminoketones Belonging to the Adamantane Group" *Pharmaceutical Chemistry Journal* 34:6 (2000).

Marchand, A.P., "Diamondoid Hydrocarbons—Delving into Nature's Bounty", *Science* 299, 52-52 (2003).

Marchand, A.P., "Polycyclic Cage Compounds: Reagents, Substrates, and Materials for the 21st Century", *Aldrichimica Acta* 28(4):95-104 (1995).

Marshall et al., "N-Arylsulfonyl-N-alkylureas", *Journal of Organic Chemistry* 23:927-929 (1958).

Marshall et al., "Further studies on N-Arylsulfonyl-N-alkylureas", *Journal of Medicinal Chemistry* 6:60-63 (1963).

McKervey, et al., "Synthetic Approaches to Large Diamondoid Hydrocarbons", *Tetrahedron* 36:9710992 (1980).

Meeuwissen et al, "Synthesis of 1-Phosphaadamantane", *Tetrahedron Letters*, 39(24):4225-4228 (1983).

Mikhailov, B.M., et al., "Organoboron Compounds", *J. Organometallic Chemistry* 250:23-31 (1983).

Mirkin, C.A., et al., "Molecular Electronics", *Annu.. Rev. Phys. Chem.* 43:719-754 (1992).

Moiseev, I.K., et al., "Reactions of Adamantanes in Electrophilic Media", *Russian Chem. Reviews* 68(12):1001-1020 (1999).

Mochizuki, Y, et al., "Polarizability of Silicon Clusters", *Chemical Physics Letters* 336, 451-456 (2001).

Mukherjee, A.K., et al., "On the Stereochemistry of the Oxidation of 5-Phenyl-2-thiaadamantane", *J. Org. Chem.* 58:7955-7957 (1993).

Newton, M.E., "Neutral ($[N_3]^0$) and Ionised ($[N_8]^+$) Single Substitutional Nitrogen in Diamond", edited by M.H. Nazare and A.J. Neves, INSPEC pp. 136-141 (2001).

Neves, A.J., et al., "Optical and EPR Properties of Transition Metals in Diamond", edited by M.H. Nazare and A.J. Neves, INSPEC pp. 167-171(2001).

Nordlander et al., "Solvolysis of 1-Adamantylcarbinyl and 3-Homoadamantyl Derivatives. Mechanism of the Neopentyl Cation Rearrangement", *Journal of the American Chemical Society* 88:19 (1966).

Okoroanyanwu, U. et al., "Alicyclic Polymers for 193 nm Resist Applications: Lithographic Evaluation", *Chem. Mater.* 10:3329-3333 (1998).

Park, H., et al., "Nanomechanical Oscillations in a Single-$C_{60}$ Transistor", *Nature* 407:57-60 (2000).

Park, S., et al., "*endo*-Fullerene and Doped Diamond Nanocrystallite-Based Models of Qubits for Solid-State Quantum Computers", *J. Nanoscience and Nanotechnology* 1(1):75-81 (2001).

Pasini, D., et al. *Advanced Materials* 12:347-351 (2000).

Pate, B.B., "The Diamond Surface: Atomic and Electronic Structure", *Surface Science* 165:83-142 (1986).

Pearsall, T.P.,ed.,"Single-Electron Transistors", pp. 8-12 from *Quantum Semiconductor Devices and Technologies*, Kluwer Academic Publishers (2000).

Pereira, E., "Photoconductivity in Diamond", edited by M.H. Nazare and A.J. Neves, INSPEC pp. 243-244 (2001).

Prins, J.F., "Large Dopants in Diamond", *Diamond*, edited by M.H. Nazare and A.J. Neves, INSPEC pp. 331-336 (2001).

Radziszewski, J.G., et al., "2-Azaadamant-1-ene and 4-Azaprotoadamant-3-ene", *J. Am. Chem.* 106:7996-7998 (1984).

Ramdas, A.K., "A1.2 Modifications to $^{12}$C-diamond by the $^{13}$C-isotope: Raman, Brillouin and Infrared Spectroscopy of Phonons", *INSPEC*, Properties, Growth and Applications of Diamondoids (2001).

Ramdas, A.K., "A1.3 Electronic Excitations in Isotopically Controlled Diamonds: Infrared and Raman Spectroscopy of Acceptor-Bound Holes", *INSPEC*, Properties, Growth and Applications of Diamondoids (2001).

Reinhardt, "Biadamantane and some if its Derivatives", *Journal of Organic Chemistry* 27:3258-3261 (1962).

Risch, N., et al., "Triple (Grob) Gragmentation. Retro-Mannish Reactions of 1-Aza-Adamantane Derivates", *Tetrahedron Letters* 32(35):4465-4468 (1991).

Risch, N., et al., "Unusual Reorganization Reactions of 3-Azabicycl[3.3.1]nonanes", *J. Am. Chem. Soc.* 113:9411-9412 (1991).

Roberts, P.J., et al., "*anti*-Tetramantane, a Large Diamondoid Fragment", *Acta. Cryst.* B33:2335-2337 (1977).

Sasaki, T. et al., "New Highly Strained Bridgehead Imines, 2-Azaadamant-1-ene and 4-Azaprotoadamant-3-ene", *Tetrahedron Letters* 23(47):4969-4972 (1982).

Sasaki, T., et al., "Synthesis and Acidolysis of 3-*endo*-Azidomethyl- and 3-*endo*-Azido-bicyclo[3.3.1]non-6-enes. A Novel Synthesis of 4-Azahomoadamant-4-enes", *J. Chem. Soc. Perkin Trans I* 2529-2534 (1983).

Saski, T., et al., "Synthesis of Adamantane Derivatives. 42. Novel Synthesis of 5-Methylene-4-azahomoadamantane Derivatives from 2-Methyl-2-hydroxyadamantane and Their Carbon-13 Nuclear Manetic Resonance Spectra", *J. Org. Chem.* 43(20):3810-3813 (1978).

Sasaki, T., et al., "Photolytic Generation of Anti-Bredt Imines from 1-Azidobicyclo[2.2.2]octane, 1-Azidobicyclo[3.3.1]nonane, and 3-Azidonoradamantane", *J. Org. Chem.* 48(22):4067-4072 (1983).

Sasaki et al., "Synthesis of Adamantane Derivatives. II. Preparation of Some Derivatives from Adamantylacetic Acid", *Bulletin of the Chemical Society of Japan* 41(1):238-240 (1968).

Sasaki et al., "Substitution Reaction of 1-Bromoadamantane in Dimethyl Sulfoxide: Simple Synthesis of 1-Azidoadamantane", *Journal of the American Chemical Society* 92:24 (1970).

Sasaki et al, "Synthesis of Adamantane Derivatives. 39. Synthesis and Acidolysis of 2-Azidoadamantanes. A Facile Route to 4-Azahomoadamant-4-enes", *Heterocycles* 7(1):315-320 (1977).

Sasaki et al, "Synthesis of Adamantane Derivatives. 47. Photochemical Synthesis of 4-Azahomoadamant-4-enes and Further Studies on Their Reactivity in Some Cycloadditions", *Journal of Organometallic Chemistry* 44(21):3711-3712 (1979).

Sasaki, T., et al., "Synthesis of Adamantane Derivatives. XII. The Schmidt Reaction of Adamanatane-2-one", *J. Org. Chem.* 35(12):4109 (1970).

Scherz, P., "Semiconductors: Chapter 4", pp. 123-190, from *Practical Electronics for Inventors*, McGraw-Hill (2000).

Service, R.F., "Can Chemists Assemble a Future for Molecular Electronics?", *Science* 295:2398-2399 (2002).

Stetter, et al., "Zur Kenntnis der Adamantan-carbonsaure-(1)", *Uber Verbidugen mit Urotropin-Struktur*, XVII, pp. 1161-1166 (1960).

Stetter, et al., "Ein Beitrag zur Frage der Reaktivitat von Bruckenkopf-Carboniumionen", *Uber Verbindungen mit Urotropin-Struktur XXVI, Chem. Ber.* 96:550-555 (1963).

Stetter, et al., "Neue Moglichkeiten der Direcktsubstitution am Adamantan", *Uber Verbindugen mit Urotropin-Struktur, XLII, Chem. Ber.* 102(10):3357-3363 (1969).

Stetter et al., "Über Adamantan-phosphonsaure-(1)-dichlorid", *Uber Verbindungen mit Urotropin-Strukture XLIV, Chem. Ber.* 102(10):3364-3366 (1969).

Stetter, et al., "Herstellung von Derivaten des 1-Phenyl-adamantans", *Uber Verbindungen mit Urotropin-Strukture, XXXI, Chem. Ber.* 97(12):3488-3492 (1964).

Stetter, H., et al., Ringschlußreaktionen ausgehend von Bicyclo[3.3.1]nonandion-(3.7) *Uber Verbindugen mit Urotropin-Strukture, XXX* 3480-3487 (1964).

Suginome, H., et al., "The Replacement of the Carbonyl Group of Adamantanone by an Oxygen or sulfur Atom and the One-step Transformation of 2-Methyladamantan-2-ol into 2-Oxa-adamantane; An Efficient New Synthesis of 2-Oxa- and 2-Thiaadamantane", *Synthesis* 741-743 (1986).

Suginome et al, "Photoinduced Transformations. 73. Transformations of Five-(and Six-) Membered Cyclic Alcohols into Five-(and Six-) Membered Cyclic Ethers-A New Method of a Two-Step Transformation of Hydroxy Steroids into Oxasteroids", *Journal of Organometallic Chemistry* 49:3753-3762 (1984).

Udding et al, "A Ring-opening Reaction of and Some Cyclisations to the Adamantane System. A Quasi-favorsky Reaction of a β-bromoketone", *Tetrahedron Letters* 55:5719-5722 (1968).

Verhoeven, J.W.., "From Close contact to Long-Range Intramolecular Electron Transfer", *Intramolecular Electron Transfer*, John Wiley and Sons, pp. 603-644 (1999).

von H.U. Daeniker, "206. 1-Hydrazinoadamantan", *Helvetica Chimica Acta* 50:2008-2010 (1967).

Yang, X. et al., "The Synthesis and Structural Characterization fo Carborane Oligomers Connected by Carbon-Carbon and Carbon-Boron Bonds Between Icosahedra", *Inorganica Chimica Acto* 240:371-378 (1995).

Zeze, D.A., et al., "Targeting Mass-Selected Cluster Ions for the Deposition of Advanced Carbonaceous Materials Using an Inductively Coupled Plasma", *Journal of Applied Physics* 91(4):1819-1827 (20020>.

Erdemir Ali, Christophe Donnet, "Tribology of Diamond, Diamond-Like Carbon, and Related Films", Chapter 24 from *Modern Tribology Handbook*, vol. 2, CRC Press, pp. 871-908 (2001).

Frommer, Jane E. and Ronald R. Chance "Electrically Conductive Polymers", *High Performance Polymers and Composites*, Jacqueline I. Kroschwitz Ed., John Wiley & Sons, New York, pp. 174-219.

Moore, Jeffrey S. and Stephen Lee, "Crafting Molecular Based Solids", *Chemistry and Industry*, pp. 556-560, Jul. 18, 1994.

Courtney T, et al. "The Chemistry of Diamantane. Part I. Synthesis and Some Functionalization Reactions", *J. Chem. Soc., Perkin Trans. 1*, 2691-2696 (1972).

Blaney, F. et al., "Chemistry of Diamantane. Part II. Synthesis of 3,5-Disubstituted Derivatives", *Synth. Commun.* 3(6):435-439 (1973).

Sasaki, Tadashi, et al., "Synthesis of Adamantane Derivatives. XII. The Schmidt Reation of Adamantan-2-one[1,2]", *J. Org. Chem.* 35(12):4109-4113 (1970).

Krishnamurthy, V.V. and Raymond C. Fort, Jr., Heteroadamantanes. 2. Synthesis of 3-Heterodiamantanes[1a,b] *J. Org. Chem.* 46(7):1388-1393 (1981).

* cited by examiner

FIG. 5B (Cont.)
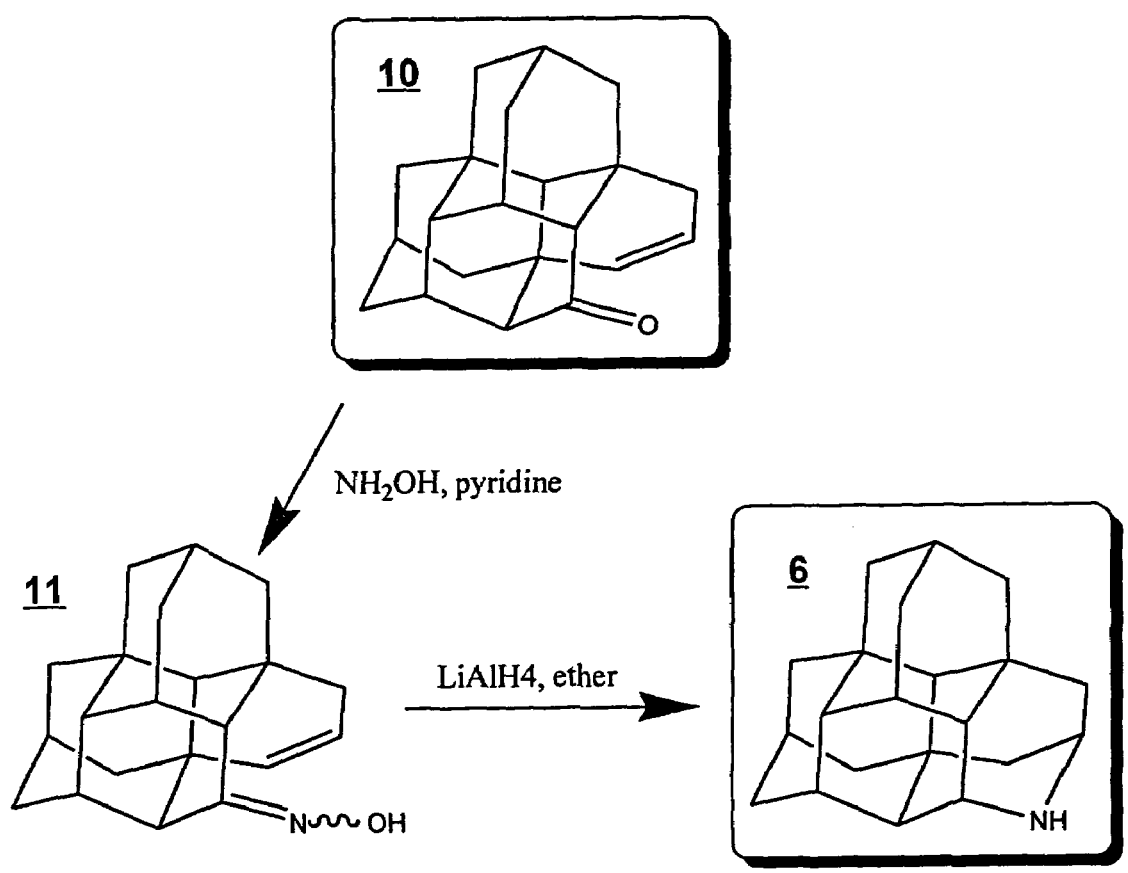

POLYACETYLENE

POLYPARAPHEMYLENE

POLYPYRROLE

POLYPARAPHEMYLENE SULPHIDE

POLYTHIOPHENE

POLYPARAPHEMYLENE VINYLENE

POLY-3 METHYL THIOPHENE

POLYCARBAZOLE

POLYISOTHIANAPHENE

POLY(1,6-HEPTADIYNE)

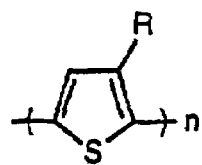
POLY-3 ALKYLTHIOPHENE
FIG. 9 K
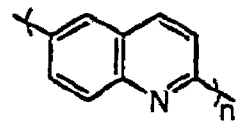
FIG. 9 L   POLYQUINOLINE
POLY-3 ALKYLSULFONATE
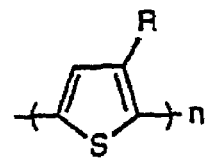
FIG. 9 M
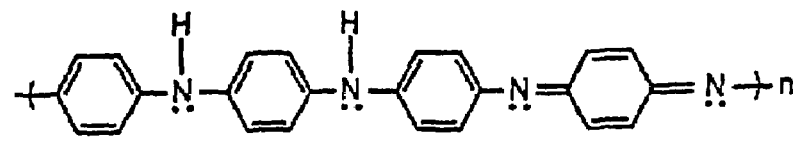
POLYANILINE
FIG. 9 N

FIG. 12
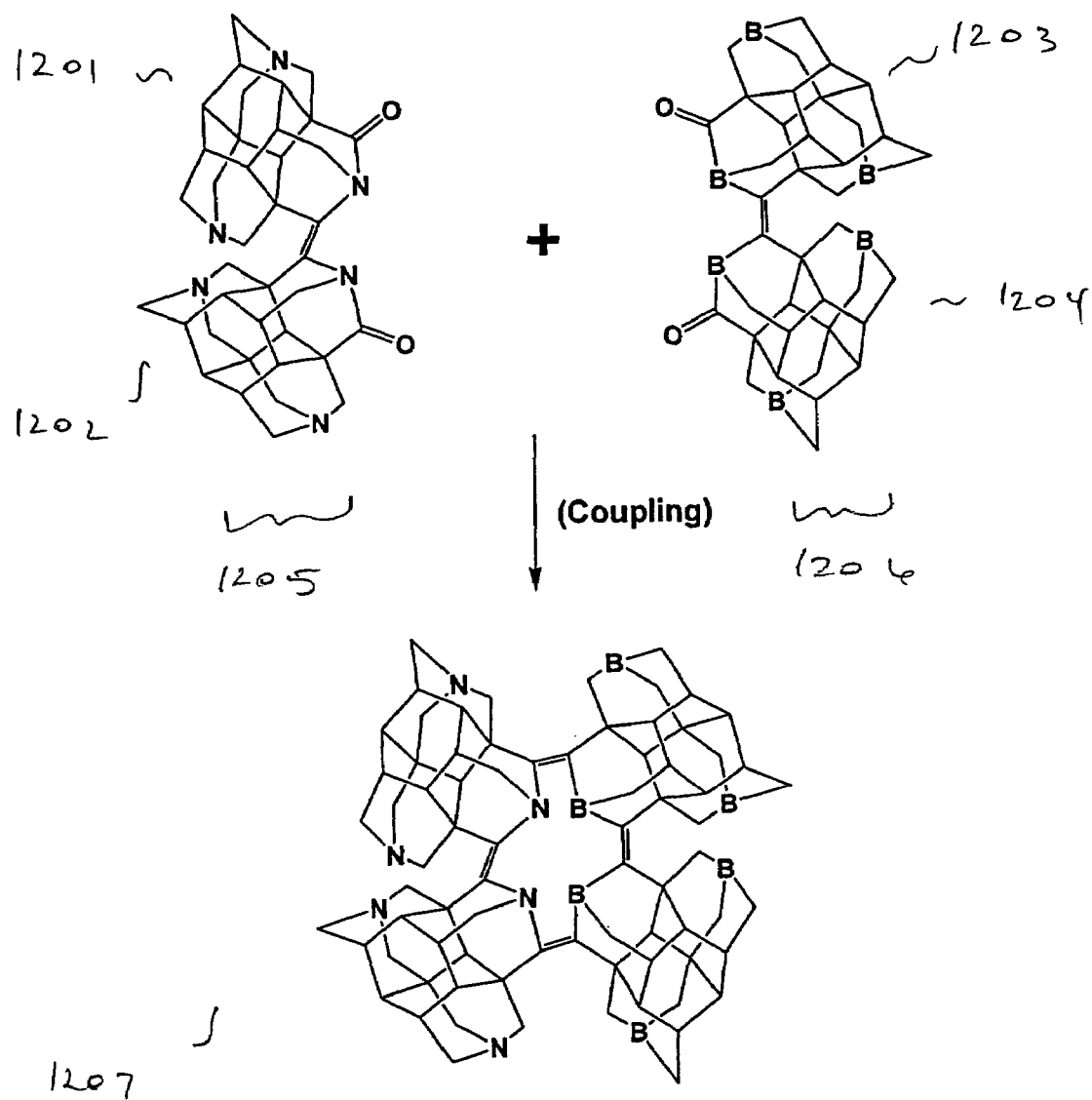

HETEROATOM-CONTAINING DIAMONDOID TRANSISTORS

REFERENCE TO RELATED APPLICATIONS

The present application claims the benefit of U.S. Provisional Patent application No. 60/397,483 filed Jul. 18, 2002. U.S. Provisional Patent application No. 60/397,483 is hereby incorporated by reference in its entirety.

BACKGROUND OF THE INVENTION

1. Field of the Invention

Embodiments of the present invention are directed in general toward n and p-type materials fabricated from heteroatom-containing diamondoids, wherein the heteroatom is an electron-donating or electron-withdrawing dopant atom substitutionally positioned within the diamond lattice structure. More particularly, the present invention is directed toward semiconducting devices that may be fabricated from such n and p-type materials, including diodes, bipolar transistors, and field effect transistors.

2. State of the Art

Carbon-containing materials offer a variety of potential uses in microelectronics. A review of carbon's structure-property relationships has been presented by S. Prawer in a chapter titled "The Wonderful World of Carbon," in *Physics of Novel Materials* (World Scientific, Singapore, 1999), pp. 205-234. Prawer suggests the two most important parameters that may be used to predict the properties of a carbon-containing material are, first, the ratio of $sp^2$ to $sp^3$ bonding in a material, and second, microstructure, including the crystallite size of the material, i.e. the size of its individual grains.

Elemental carbon has the electronic structure $1s^2 2s^2 2p^2$, where the outer shell 2s and 2p electrons have the ability to hybridize according to two different schemes. The so-called $sp^3$ hybridization comprises four identical σ bonds arranged in a tetrahedral manner. The so-called $sp^2$-hybridization comprises three trigonal (as well as planar) σ bonds with an unhybridized p-electron occupying a π orbital in a bond oriented perpendicular to the plane of the σ bonds. At the "extremes" of crystalline morphology are diamond and graphite. In diamond, the carbon atoms are tetrahedrally bonded with $sp^3$-hybridization. Graphite comprises planar "sheets" of $sp^2$-hybridized atoms, where the sheets interact weakly through perpendicularly oriented π bonds. Carbon exists in other morphologies as well, including amorphous forms called "diamond-like carbon" (DLC), and the highly symmetrical spherical and rod-shaped structures called "fullerenes" and "nanotubes," respectively.

Diamond is an exceptional material because it scores highest (or lowest, depending on one's point of view) in a number of different categories of properties. Not only is it the hardest material known, but it has the highest thermal conductivity of any material at room temperature. It displays superb optical transparency from the infrared through the ultraviolet, has the highest refractive index of any clear material, and is an excellent electrical insulator because of its very wide bandgap. It also displays high electrical breakdown strength, and very high electron and hole mobilities.

Bulk diamond is an insulator, and does not become a semiconductor until electron-donating or electron-withdrawing impurity atoms are inserted into the diamond lattice. Such impurity atoms usually come from group IIIA or IVA (using the present day IUPAC nomenclature) of the periodic table. Prior art methods of introducing dopant atoms into diamond include in situ insertion during growth (usually growth obtained by CVD), or ex situ insertion, such as by ion implantation or by high temperature diffusion.

Ion implantation of diamond has been discussed by R. Kalish and C. Uzan-Saguy in chapter B3.1, titled "Doping of diamond using ion implantation," in *Properties, Growth and Applications of Diamond*, edited by M. H. Nazaré and A. J. Neves (Inspec, London, 2001), pp. 321-330. A disadvantage of the ion implantation technique, however, is that it forces atoms into the crystal regardless of solubility or diffusivity characteristics of the atoms being inserted. This is a violent procedure that is accompanied by bond breakage and the creation of defects in the material. Unless removed by proper annealing, these defects may lead to undesirable electronic states that overshadow the desired chemical effects of the doping. However, it is more difficult to anneal diamond than it is to anneal other group IV semiconductors, such as silicon, because of the metastability of diamond bonding ($sp^3$). Broken $sp^3$-hybridized diamond bonding can rearrange to the more stable and electrically conductive $sp^2$ bonding of graphite.

Some sort of annealing is necessary, on the other hand, because broken $sp^3$ bonds and related defects caused by the implantation process can lead to electrical effects which may be mistaken for the desired chemical doping. A few of the undesirable electrical effects that may result from implanting dopants into diamond include the creation of energy levels within the bandgap which may give rise to the desired donor or acceptors states, or compensate desired doping levels; the creation of electrically conducting pathways by creating $sp^2$ bonded states or clusters, the creation of scattering centers which may limit or reduce carrier mobilities; and finally, the creation of dopant defect complexes which may passivate the dopants.

Disadvantages of prior art methods may include the anisotropy in the electrical properties of a doped diamond material fabricated using CVD methods. For example, in the case of n-type diamond, the addition of nitrogen to CVD grown diamond results in the enhancement of the growth rate of (100) faces, with decreasing growth rates on (111) and (110) faces. In a similar manner, the probability of boron incorporation in <111> oriented films is up to an order of magnitude higher than in <100> films. This has been discussed by G. Z. Cao in chapter B3.4, titled "Nitrogen and phosphorus doping in CVD diamond," in *Properties, Growth and Applications of Diamond*, edited by M. H. Nazaré and A. J. Neves (Inspec, London, 2001), pp. 345-347.

Another disadvantage of the prior art methods, also discussed by R. Kalish and C. Uzan-Saguy, is that while ion implantation is accompanied by bond breakage that has to be removed by annealing, the annealing of diamond cannot be done at sufficiently high temperatures to be effective because otherwise metastable $sp^3$-hybridized carbon would revert to the more stable $sp^2$-hybridized graphite. Thus, the observation of an n-type electrical semiconduction is not often observed in diamond. This is the case particularly for nitrogen as a dopant, and probably for phosphorus, lithium, and arsenic as well.

What is needed is an n or p-type diamond-like material with desired mechanical and electrical properties, where no implantation-created crystal defects are created that may lead to undesired electronic states. The n-type diamondoid-based materials of the present invention may show more favorable electrical characteristics than implanted diamond. The n and p-type diamondoid materials of the present material may be used in devices having p-n junctions, such as diodes, transistors, including single electron transistors.

A form of carbon not discussed extensively in the literature is the "diamondoid." Diamondoids are bridged-ring cycloalkanes that comprise adamantane, diamantane, triamantane, and the tetramers, pentamers, hexamers, heptamers, octamers, nonamers, decamers, etc., of adamantane (tricyclo [$3.3.1.1^{3,7}$] decane), adamantane having the stoichiometric formula $C_{10}H_{16}$, in which various adamantane units are face-fused to form larger structures. These adamantane units are essentially subunits of diamondoids. The compounds have a "diamondoid" topology in that their carbon atom arrangements are superimposable on a fragment of an FCC (face centered cubic) diamond lattice. According to embodiments of the present invention, electron donating and withdrawing heteroatoms may be inserted into the diamond lattice, thereby creating an an n and p-type (respectively) material. The heteroatom is essentially an impurity atom that has been "folded into" the diamond lattice, and thus many of the disavantages of the prior art methods have been avoided.

SUMMARY OF THE INVENTION

For diamond to be useful in a semiconductor device, it needs to be electrically conductive, and thus it is necessary to dope diamond with impurity atoms that act as either electron donors or acceptors. However, doping diamond is not an easy task, due to the tightness and strength of the diamond lattice, and it can be difficult to form ohmic contacts to this wide bandgap semiconductor. Common methods for including impurity atoms into diamond include hot filament CVD and ion implantation techniques.

Ion implantation causes extensive damage to the diamond crystal lattice because the doping atoms are forced into the crystal, regardless of solubility or diffusivity considerations. Ion implantation is often accompanied by the creation of defects in the wake of the implanted ions. To repair the damage, the material needs to be annealed, but the annealing of diamond is more complex than the annealing of other group IV semiconductors (such as silicon) due to the metastable condition of diamond $sp^3$ bonding versus graphitic $sp^2$ bonding. Tetradetral bonds that are broken during the implantation process, and other crystal defects such as dislocations, can give rise to electrical effects that interfere with the desired properties one is trying to impart to the crystal.

According to embodiments of the present invention, diamondoids are isolated from petroleum feedstocks, and heterodiamondoids are synthesized by substitutionally positioning heteroatoms onto host carbon positions of the diamond lattice. These heteroatoms in general come from groups III and V of the periodic table, and in general, comprise electron-withdrawing and electron-donating entities, respectively. Examples of group III electron-withdrawing impurity atoms include boron and aluminum. Examples of group V electron-donating impurity atoms include nitrogen, phosphorus, and arsenic, although lithium and sodium may be used as well.

Once the heterodiamondoids containing electron-donating and electron-withdrawing heteroatoms have been synthesized, the heterodiamondoids may be fabricated into n and p-type materials. These n and p-type materials may be fabricated using a variety of techniques, including chemical vapor deposition (CVD), polymerization, crystallization, and the like. Using CVD techniques, heterodiamondoids may injected into a CVD reactor to nucleate diamond growth, whereby the heteroatom of the heterodiamondoid is included into a growing diamond film with the damage created by implantation methods. In an alternative embodiment, heterodiamondoids may be functionalized with polymerizable substitutents to link adjacent diamondoids and/or heterodiamondoids together. The linking groups may be short lengths (oligomers or even monomers) of conductive polymers known in the art. Heterodiamondoids may also be used as "molecular crystals," where arrangements of diamondoid and heterodiamondoid molecules are packed together in a "superlattice," and where the diamondoids are held together by van der Waals forces.

The n and p-type diamondoid-containing materials may then be used in semiconductor devices that utilize p-n junctions known in the art. Such devices include rectifying diodes, bipolar junction transistors, and field effect transistors.

BRIEF DESCRIPTION OF THE DRAWINGS

FIG. 12 shows how individual heterodiamondoids may be coupled to form an n or p-type device at the molecular level;

DETAILED DESCRIPTION OF THE INVENTION

According to embodiments of the present invention, n and p-type heterodiamondoid based materials may be used in a variety of microelectronic devices. In some embodiments of the contemplated devices, it is the properties of a p-n junction formed between the two types of materials that is being exploited. An overview of exemplary methods and devices of the present invention is presented in FIG. 1.

Figure 1:
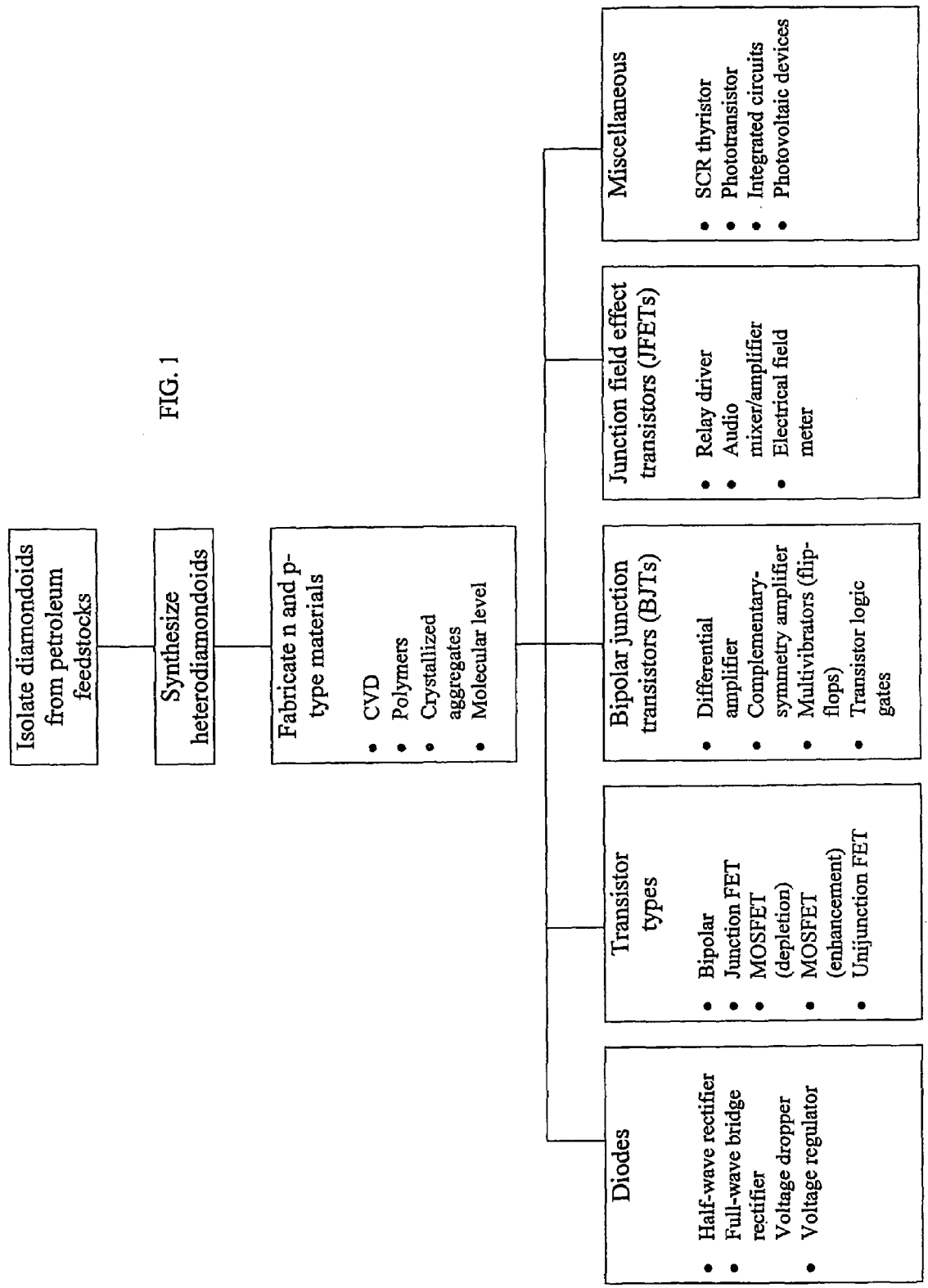
FIG. 1 is an overview of the embodiments of the present invention, showing the steps of isolating diamondoids from petroleum, synthesizing heterodiamondoids, preparing n and p-type materials therefrom, and creating microelectronic devices that utilize p-n junctions.

Referring to FIG. 1, n and p-type heterodiamondoid materials are created first by synthesizing individual heterodiamondoid molecules from the corresponding diamondoid with no heteroatom, and then fabricating a bulk n or p-type material from the heterodiamondoid. Exemplary fabrication steps include, but are not limited to, CVD techniques, polymerization, and the use of the heterodiamondoids in an aggregated or packed condition. In quantum dot technologies (such as single electron transistors), the device may comprise a small number of heterodiamondoids used either individually or in conjunction with one another.

This disclosure is organized as follows: a) a description of properties of n and p-type diamond, including examples of impurity atoms that have been used to dope diamond, b) a definition of the term "diamondoid," c) a brief description of how diamondoids may be recovered from petroleum feedstocks, and the various diamondoid isomers that are available, d) exemplary synthetic methods for introducing a heteroatom into a diamondoid such that the heteroatom substitutionally occupies a lattice site in the diamond structure (resulting in a "heterodiamondoid"), e) methods for converting individual heterodiamondoid molecules into bulk n and p-type materials, including chemical vapor deposition (CVD), polymerization, and aggregation into larger sized crystals by Van der Waals packing, and f) exemplary microelectronic devices contemplated to make use of the present n and p-type diamondoid materials and p-n junctions formed therefrom, including rectifying diodes, bipolar junction transistors, and field effect transistors.

Properties of n and p-type Diamond

To date, the well-known impurity atoms that have been used to dope diamond include boron and nitrogen. Boron is a p-type dopant with an activation energy of 0.37 eV. Nitrogen is an n-type impurity which may be referred to as a deep donor, because it has the energy level 1.7 eV away from the bottom of the conduction band. Because boron and nitrogen are adjacent to carbon in the same row of the periodic table, these atoms have similar sizes, and thus may be readily introduced into the crystal if size considerations only are taken into account. The properties of boron and nitrogen doped diamond, in particular as they relate to ion implantation, have been discussed by R. Kalish and C. Uzan-Saguy in chapter B3.1, titled "Doping of diamond using ion implantation," in *Properties, Growth and Applications of Diamond*, edited by M. H. Nazaré and A. J. Neves (Inspec, London, 2001), pp. 321-330.

In the past, greater success has been achieved developing a p-type diamond material than an n-type material. Satisfactory doping of diamond with nitrogen has proven to be elusive, although there has been some recent success with hot filament CVD methods. Recently it has been demonstrated by CVD methods that phosphorus has a donor state in the diamond bandgap, with a reported activation energy ranging from about 0.46 to 0.6 eV.

Boron containing diamond exists in nature (it is called type IIb natural diamond), and its electrical properties have been studied extensively. These studies show that the activation energy level of the boron accepter is positioned 0.37 eV above the valence band. More recently, boron doped p-type diamonds have been made using both high-pressure high temperature (HPHT) and chemical vapor deposition (CVD) techniques. The best p-type diamond material made to date has apparently been made by CVD epitaxial growth on <100> diamond surfaces. These materials have been reported to yield a carrier mobility of 1800 $cm^2V^{-1}s_{-1}$, and a carrier concentration of about $2.3 \times 10^{14}$ $cm^{-3}$ at room temperature. It has been postulated that the success of fabricating boron doped p-type diamond is due to the small size of the boron atom, which enables it to enter the diamond lattice easily. Once inside the lattice it occupies a predominance of substitutional sites (as opposed to interstitial sites), where electrically it acts as an electron accepter.

Kalish and Uzan-Saguy summarize the main points about p-type diamond by saying that boron is the best studied p-type dopant in diamond. The boron doped materials demonstrate hole mobilities up to 600 $cm^2/Vs$, and compensation ratios below 5 percent. The optimal annealing scheme was found to be a high temperature anneal at a temperature greater than 1400° C.

In contrast to p-type diamond, n-type diamond has been more difficult to fabricate. Among the potential substitutional donors for diamond, only nitrogen and phosphorus appear to enter the crystal to contribute to its electrical properties. Both elements may be introduced into diamond during CVD growth. Additionally, group I elements occupying interstitial sites, such as sodium and lithium, have been predicted to act as donors with activation energies of 0.1 and 0.3 eV, respectively. The energy of formation for the bonding of nitrogen within the carbon lattice is predicted to be negative, −3.4 eV, in contrast to the high positive energies of formation predicted for phosphorus (10.4 eV), lithium (5.5 eV), and sodium (15.3 eV). This suggests that the solubilities of these elements in diamond is low, with the exception of nitrogen.

As with boron, nitrogen also exists substitutionally in natural diamond (type Ib diamond), where the impurity has an activation energy of 1.7 eV. Since this is a very high ionization energy, diamond containing nitrogen impurities are electrically insulating at room temperature, and thus these materials cannot be studied by conventional electrical measurement techniques. Using implantation techniques similar to those used for boron, it was found that after annealing about 50 percent of the implanted nitrogen was located in substitutional sites, but that the nature of the depth of the energy level rendered this type of material unsuitable for use at room temperature.

Phosphorus has been predicted to act as a shallow donor in diamond, phosphorus having an activation energy of 0.1 eV. Recently, however, phophorus doped diamond has been grown by CVD techniques, and Hall effect measurements showed that phosphorus produced a donor level with an ionization energy about 0.5 eV below the bottom of the conduction band. The mobility of carriers in this material was found to be between about 30 and 180 $cm^2V^{-1}s^{-1}$, and typical room temperature carrier concentrations were found to be on the order of $10^{13}$ to $10^{14}$ $cm^{-3}$. In other studies, it was found that phosphorus occupied substitutional sites about 70 percent of the time following an anneal at 1200° C.

Although this appears to be an attractive method of producing n-type diamond, the authors stated that n-type electrical activity of ion implanted phosphorus in diamond has not been found. The cause was speculated to be the large size of the phosphorus atom relative to the dimensions of the diamond crystal lattice. The misfit induces a strain in the diamond lattice which appears to attract and create defects with no electrical activity.

Attempts have also been made to produce n-type diamond by lithium implantation. In one study, n-type conductivity was verified by hot probe measurements, with an activation energy of 0.23 eV. Another study found an activation energy of 0.22 eV. In another study, about 40 percent of the implanted lithium was found to occupy interstitial lattice sites, with 17 percent in substitutional sites, but no clear n-type electrical signal could be found in this case. It was postulated that substitutional lithium acts as accepter, and interstitial lithium behaves as a donor, with possible compensation between the two effects resulting in no electrical activity.

A further discussion of boron doped diamond has been given by C. Johnston et al. in chapter B3.3, titled "Boron doping and characterization of diamond," in *Properties,*

Growth and Applications of Diamond, edited by M. H. Nazaré and A. J. Neves (Inspec, London, 2001), pp. 337-344. These authors state that it is known from studies on natural diamond that boron acts as an acceptor with an energy level 0.368 eV above the edge of the valence band. There are essentially three ways to achieve the doping of diamond with boron, and these methods include 1) incorporation of boron in diamond in situ during growth, 2) ex situ by ion implantation, and 3) by high temperature diffusion. One disadvantage with the above mentioned methods is that boron incorporation may be dependent upon the texture of the diamond film or the orientation of the substrate upon which the diamond is being deposited. In one study, the probability of boron incorporation into a growing diamond film having a having <111> orientation was up to one order of magnitude greater than in films having a <100> orientation. The incorporation of dopants into a growing diamond film is also dependent upon the morphology of the deposited material. For example, the average crystallite size was reduced by an order of magnitude when the boron concentration was increased from about $10^{16}$ to $10^{21}$ cm$^{-3}$.

As discussed above, it is more difficult to prepare n-type diamond than p-type diamond by ion implantation, but recently the incorporation of nitrogen and phosphorus into diamond using CVD methods have proven to be more successful. Such a technique has been discussed by G. Z. Cao in chapter B3.4, titled "Nitrogen and phosphorus doping in CVD diamond," in *Properties, Growth and Applications of Diamond*, edited by M. H. Nazaré and A. J. Neves (Inspec, London, 2001), pp. 345-347. This author states that diamond promises high power, high frequency, and high temperature electronic applications due to its unique physical properties. These properties include a high carrier mobility of 0.16 m²/Vs, a high thermal conductivity of up to about 1.5×10⁴ W/m K, and a wide bandgap energy of 5.5 eV. P-type conduction has been demonstrated in both the naturally occurring type IIb diamond, as well as synthetic p-type diamond created by either high pressure, high temperature (HPHT) techniques or by chemical vapor deposition CVD techniques. To create n-type diamond, nitrogen and phosphorus were considered to be possible donor elements.

Nitrogen is the most prevalent impurity in naturally occurring diamond, and can be readily incorporated into CVD diamond using either $N_2$ or $NH_3$ as a precursor. Hot filament CVD was the preferred method. Typical concentrations were 6×10¹⁹ atoms/cm³. However, the rate of incorporation of nitrogen into the growing diamond film was dependent on the orientation of the growing film, and the growth rate of the film was dependent on the amount of nitrogen in the feed gas. For example, (100) facets incorporated the highest concentration of nitrogen into the diamond, followed by (111) facets, with (100) facets incorporating the least amount of nitrogen. However, the addition of nitrogen to the feed gas resulted in the greatest enhancement of growth for (100) facets, followed by (111) facets, with the least enhancement in (110) facets.

Cao reiterates that phosphorus is a promising donor candidate for n-type semiconducting diamond films. Modelling has shown that phosphorus may behave as a shallow donor in diamond, having an energy level 0.2 eV from the bottom of the conduction band. However, phosphorus has a large positive energy of formation (10.4 eV), and thus a low equilibrium solubility in diamond. This is in part due to the large size of phosphorus relative to carbon; for example, phosphorus has a radius of 1.10 angstroms compared to the 0.77 angstrom radius of carbon.

In early studies of phosphorus doping, only low concentrations of phosphorus doping could be achieved, but it was found that the concentrations of phosphorus could be enhanced in the presence of other impurities, such as boron. Unfortunately, due to the donor-acceptor compensation effect discussed above, no n-type conduction could be achieved.

To review: the properties of of the doped diamond depend on the nature of the dopant. Boron doped diamond has an acceptor level of 0.368 eV above the valence band, which may be viewed as a shallow level, and therefore holes may be excited from states within the bandgap to the top of the valence band with relatively low energies. However, nitrogen is a deep donor with an energy level 1.7 eV away from the bottom of the conduction band, and therefore relatively large amounts of energy are required to elevate an electron from a donor state within the conduction band to the bottom of the conduction band. Thus, when n-type diamond is doped with diamond, it is not electrically conducting at room temperature because these temperature do not provide enough energy to excite the electron from its energy state state within the bandgap to the conduction band. Phosphorus has been modelled to be a shallow donor with an energy state at 0.2 eV away from the conduction band edge, making phosphorus a potential candidate for an n-type dopant, and lithium is another possiblity.

It should be noted that, under some circumstances, the hydrogenated surface of diamond may impart to the crystal a p-type conductivity. This has been discussed by K. Bobrov et al. in "Atomic-scale imaging of insulating diamond through resonant electron injection," *Nature*, Vol. 413, pp. 616-619 (2001). This study demonstrated that a scanning tunnelling microscopic technique could be used to image an "insulating" diamond surface to investigate electronics properties at the atomic scale. The hydrogenated surface of a single crystal of (100) diamond could be imaged with STM at a negative sample bias. The hydrogen-free diamond surface was insulating.

Embodiments of the present invention circumvent the difficulties of the prior art techniques by synthesizing heterodiamondoids such that the impurity donor or acceptor atom is included in the diamond crystal lattice structure prior to the fabrication of the n or p-type semiconducting material. Such n and p-type heterodiamondoid materials may be used in devices, for example, that utilize a p-n junction. These devices include transistors having n-p-n and p-n-p sandwiched layers of semiconducting diamondoid materials. Diamondoids that do not contain heteroatoms may be useful as p-type materials (see discussion by Bobrov above) because the surface of these hydrocarbon molecules is hydrogenated.

Definition of Heterodiamondoids

The term "diamondoids" refers to substituted and unsubstituted caged compounds of the adamantane series including adamantane, diamantane, triamantane, tetramantane, pentamantane, hexamantane, heptamantane, octamantane, nonamantane, decamantane, undecamantane, and the like, including all isomers and stereoisomers thereof. The compounds have a "diamondoid" topology, which means their carbon atom arrangement is superimposable on a fragment of an FCC diamond lattice. Substituted diamondoids comprise from 1 to 10 and preferably 1 to 4 independently-selected alkyl substituents.

Adamantane chemistry has been reviewed by Fort, Jr. et al. in "Adamantane: Consequences of the Diamondoid Structure," *Chem. Rev.* vol. 64, pp. 277-300 (1964). Adamantane is the smallest member of the diamondoid series and may be thought of as a single cage crystalline subunit. Diamantane contains two subunits, triamantane three, tetramantane four, and so on. While there is only one isomeric form of adamantane, diamantane, and triamantane, there are four different isomers of tetramantane (two of which represent an enantiomeric pair), i.e., four different possible ways of arranging the four adamantane subunits. The number of possible isomers increases non-linearly with each higher member of the diamondoid series, pentamantane, hexamantane, heptamantane, octamantane, nonamantane, decamantane, etc.

Adamantane, which is commercially available, has been studied extensively. The studies have been directed toward a number of areas, such as thermodynamic stability, functionalization, and the properties of adamantane-containing materials. For instance, the following patents discuss materials comprising adamantane subunits: U.S. Pat. No. 3,457,318 teaches the preparation of polymers from alkenyl adamantanes; U.S. Pat. No. 3,832,332 teaches a polyamide polymer forms from alkyladamantane diamine; U.S. Pat. No. 5,017,734 discusses the formation of thermally stable resins from adamantane derivatives; and U.S. Pat. No. 6,235,851 reports the synthesis and polymerization of a variety of adamantane derivatives.

In contrast, the diamondoids tetramantane and higher have received comparatively little attention in the scientific literature. McKervey et al. have reported the synthesis of anti-tetramantane in low yields using a laborious, multistep process in "Synthetic Approaches to Large Diamondoid Hydrocarbons," *Tetrahedron,* vol. 36, pp. 971-992 (1980). To the inventors' knowledge, this is the only higher diamondoid that has been synthesized to date. Lin et al. have suggested the existence of, but did not isolate, tetramantane, pentamantane, and hexamantane in deep petroleum reservoirs in light of mass spectroscopic studies, reported in "Natural Occurrence of Tetramantane ($C_{22}H_{28}$), Pentamantane ($C_{26}H_{32}$) and Hexamantane ($C_{30}H_{36}$) in a Deep Petroleum Reservoir," *Fuel,* vol. 74(10), pp. 1512-1521 (1995). The possible presence of tetramantane and pentamantane in pot material after a distillation of a diamondoid-containing feedstock has been discussed by Chen et al. in U.S. Pat. No. 5,414,189.

The four tetramantane structures are iso-tetramantane [1(2)3], anti-tetramantane [121] and two enantiomers of skew-tetramantane [123], with the bracketed nomenclature for these diamondoids in accordance with a convention established by Balaban et al. in "Systematic Classification and Nomenclature of Diamond Hydrocarbons-I," *Tetrahedron* vol. 34, pp. 3599-3606 (1978). All four tetramantanes have the formula $C_{22}H_{28}$ (molecular weight 292). There are ten possible pentamantanes, nine having the molecular formula $C_{26}H_{32}$ (molecular weight 344) and among these nine, there are three pairs of enantiomers represented generally by [12(1)3], [1234], [1213] with the nine enantiomeric pentamantanes represented by [12(3)4], [1(2,3)4], [1212]. There also exists a pentamantane [1231] represented by the molecular formula $C_{25}H_{30}$ (molecular weight 330).

Hexamantanes exist in thirty nine possible structures with twenty eight having the molecular formula $C_{30}H_{36}$ (molecular weight 396) and of these, six are symmetrical; ten hexamantanes have the molecular formula $C_{29}H_{34}$ (molecular weight 382) and the remaining hexamantane [12312] has the molecular formula $C_{26}H_{30}$ (molecular weight 342).

Heptamantanes are postulated to exist in 160 possible structures with 85 having the molecular formula $C_{34}H_{40}$ (molecular weight 448) and of these, seven are achiral, having no enantiomers. Of the remaining heptamantanes 67 have the molecular formula $C_{33}H_{38}$ (molecular weight 434), six have the molecular formula $C_{32}H_{36}$ (molecular weight 420) and the remaining two have the molecular formula $C_{30}H_{34}$ (molecular weight 394).

Octamantanes possess eight of the adamantane subunits and exist with five different molecular weights. Among the octamantanes, 18 have the molecular formula $C_{34}H_{38}$ (molecular weight 446). Octamantanes also have the molecular formula $C_{38}H_{44}$ (molecular weight 500); $C_{37}H_{42}$ (molecular weight 486); $C_{36}H_{40}$ (molecular weight 472), and $C_{33}H_{36}$ (molecular weight 432).

Nonamantanes exist within six families of different molecular weights having the following molecular formulas: $C_{42}H_{48}$ (molecular weight 552), $C_{41}H_{46}$ (molecular weight 538), $C_{40}H_{44}$ (molecular weight 524, $C_{38}H_{42}$ (molecular weight 498), $C_{37}H_{40}$ (molecular weight 484) and $C_{34}H_{36}$ (molecular weight 444).

Decamantane exists within families of seven different molecular weights. Among the decamantanes, there is a single decamantane having the molecular formula $C_{35}H_{36}$ (molecular weight 456) which is structurally compact in relation to the other decamantanes. The other decamantane families have the molecular formulas: $C_{46}H_{52}$ (molecular weight 604); $C_{45}H_{50}$ (molecular weight 590); $C_{44}H_{48}$ (molecular weight 576); $C_{42}H_{46}$ (molecular weight 550); $C_{41}H_{44}$ (molecular weight 536); and $C_{38}H_{40}$ (molecular weight 496).

Undecamantane exists within families of eight different molecular weights. Among the undecamantanes there are two undecamantanes having the molecular formula $C_{39}H_{40}$ (molecular weight 508) which are structurally compact in relation to the other undecamantanes. The other undecamantane families have the molecular formulas $C_{41}H_{42}$ (molecular weight 534); $C_{42}H_{44}$ (molecular weight 548); $C_{45}H_{48}$ (molecular weight 588); $C_{46}H_{50}$ (molecular weight 602); $C_{48}H_{52}$ (molecular weight 628); $C_{49}H_{54}$ (molecular weight 642); and $C_{50}H_{56}$ (molecular weight 656).

The term "heterodiamondoid" as used herein refers to a diamondoid that contains a heteroatom typically substitutionally positioned on a lattice site of the diamond crystal structure. A heteroatom is an atom other than carbon, and according to present embodiments may be nitrogen, phosphorus, boron, aluminium, lithium, and arsenic. "Substitutionally positioned" means that the heteroatom has replaced a carbon host atom in the diamond lattice. Although most heteroatoms are substitutionally positioned, they may in some cases be found in interstitial sites as well. As with diamondoids, a heterodiamondoid may be functionalized or derivatized; such compounds may be referred to as substituted heterodiamondoids. In the present disclosure, an n-type or p-type diamondoid typically refers to a an n-type or p-type heterodiamondoid, but in some cases the n or p-type material may comprise diamondoids with no heteroatom.

Although heteroadamantane and heterodiamantane compounds have been reported in the literature, to the inventors' knowledge, no heterotriamantane or higher compounds have been previously synthesized, and there is no reported case of the use of a heterodiamondoid, including heteroadamantane or heterodiamantane compounds as n-type or p-type materials in a semiconductor device such as a diode or a transistor. Inventors' contemplate the use of 1) heteroadamantane and heterodiamantane, or 2) heterotriamantane, or 3) heterotetramantane and above as potential transistor materials; however, n and p-type materials comprising the heterodiamondoids from tetramantane and above are expected to have advantages due to the higher carbon-to-hydrogen ratios, (where more carbons are in quaternary positions where they are bonded only to other carbons), and there are mechanical advantages as well.

Figure 2:
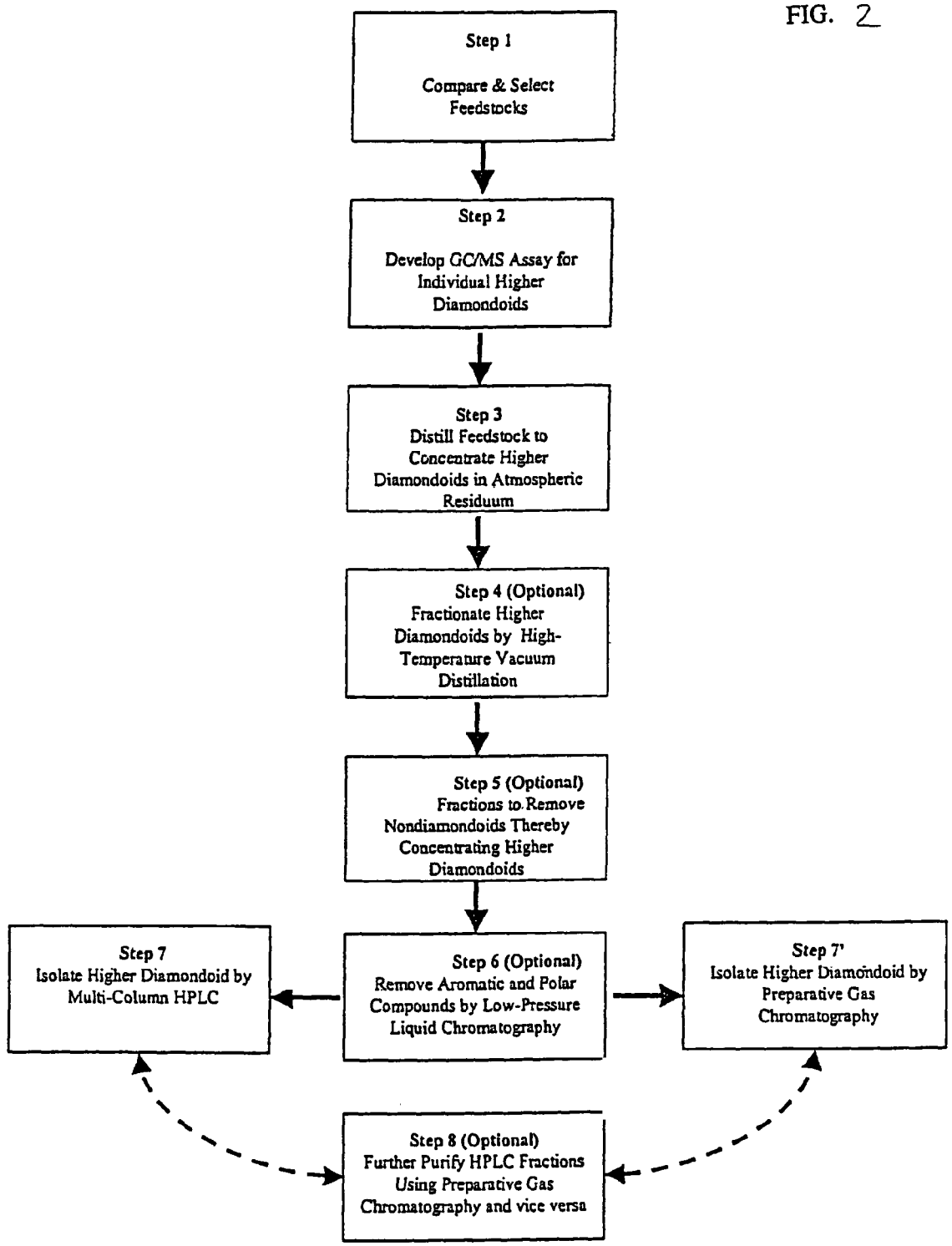
FIG. 2 shows an exemplary process flow for isolating diamondoids from petroleum.
Figure 3:
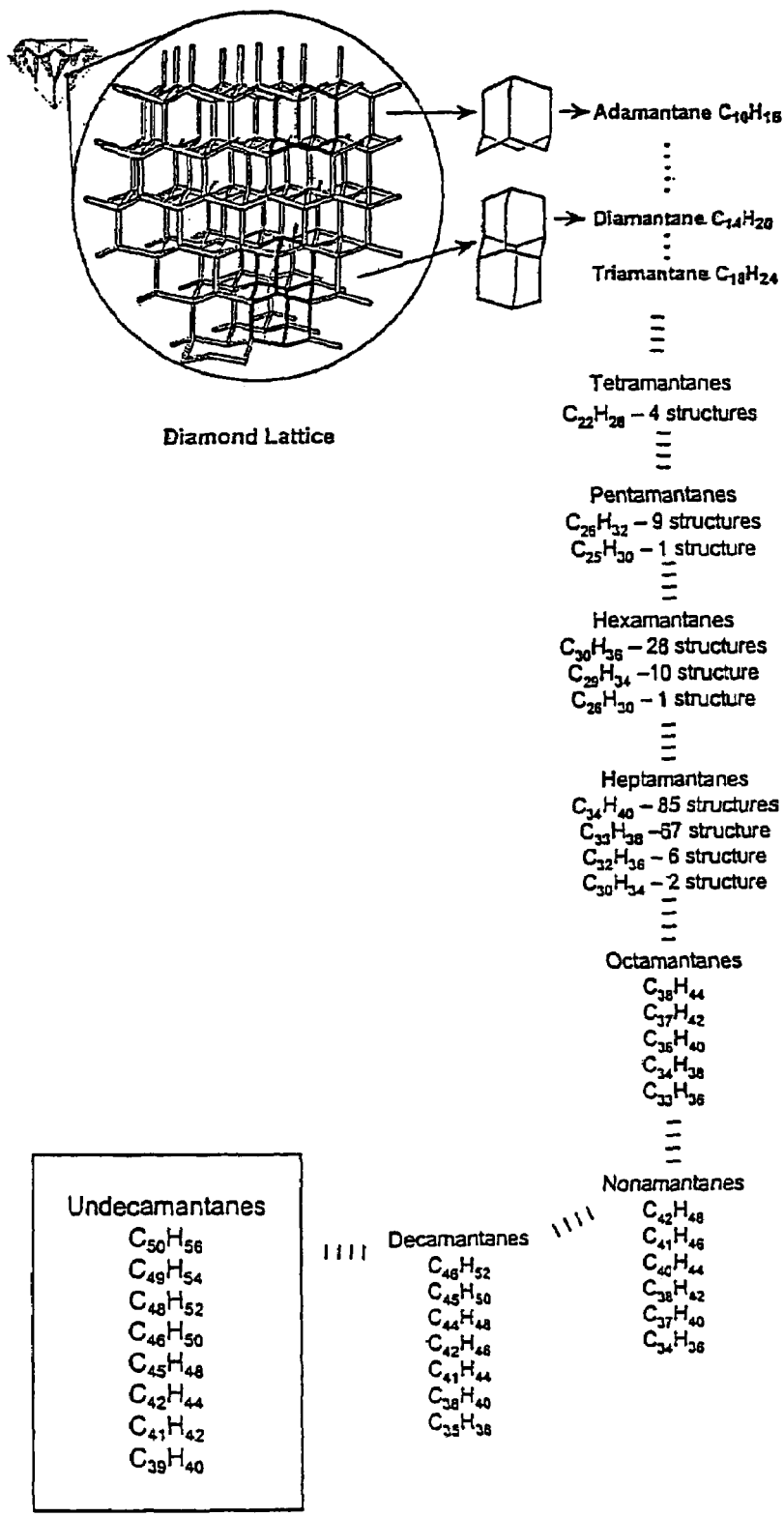
FIG. 3 illustrates the relationship of a diamondoid to the diamond crystal lattice, and enumerates many of the diamondoids available by stoichiometric formula.

FIG. 2 shows a process flow illustrated in schematic form, wherein diamondoids may be extracted from petroleum feedstocks, and FIG. 3 enumerates the various diamondoid isomers that are available from embodiments of the present invention.

Isolation of Diamondoids from Petroleum Feedstocks

Feedstocks that contain recoverable amounts of higher diamondoids include, for example, natural gas condensates and refinery streams resulting from cracking, distillation, coking processes, and the like. Particularly preferred feedstocks originate from the Norphlet Formation in the Gulf of Mexico and the LeDuc Formation in Canada.

These feedstocks contain large proportions of lower diamondoids (often as much as about two thirds) and lower but significant amounts of higher diamondoids (often as much as about 0.3 to 0.5 percent by weight). The processing of such feedstocks to remove non-diamondoids and to separate higher and lower diamondoids (if desired) can be carried out using, by way of example only, size separation techniques such as membranes, molecular sieves, etc., evaporation and thermal separators either under normal or reduced pressures, extractors, electrostatic separators, crystallization, chromatography, well head separators, and the like.

A preferred separation method typically includes distillation of the feedstock. This can remove low-boiling, non-diamondoid components. It can also remove or separate out lower and higher diamondoid components having a boiling point less than that of the higher diamondoid(s) selected for isolation. In either instance, the lower cuts will be enriched in lower diamondoids and low boiling point non-diamondoid materials. Distillation can be operated to provide several cuts in the temperature range of interest to provide the initial isolation of the identified higher diamondoid. The cuts, which are enriched in higher diamondoids or the diamondoid of interest, are retained and may require further purification. Other methods for the removal of contaminants and further purification of an enriched diamondoid fraction can additionally include the following nonlimiting examples: size separation techniques, evaporation either under normal or reduced pressure, sublimation, crystallization, chromatography, well head separators, flash distillation, fixed and fluid bed reactors, reduced pressure, and the like.

The removal of non-diamondoids may also include a thermal treatment step either prior or subsequent to distillation. The thermal treatment step may include a hydrotreating step, a hydrocracking step, a hydroprocessing step, or a pyrolysis step. Thermal treatment is an effective method to remove hydrocarbonaceous, non-diamondoid components from the feedstock, and one embodiment of it, pyrolysis, is effected by heating the feedstock under vacuum conditions, or in an inert atmosphere, to a temperature of at least about 390° C., and most preferably to a temperature in the range of about 410 to 450° C. Pyrolysis is continued for a sufficient length of time, and at a sufficiently high temperature, to thermally degrade at least about 10 percent by weight of the non-diamondoid components that were in the feed material prior to pyrolysis. More preferably at least about 50 percent by weight, and even more preferably at least 90 percent by weight of the non-diamondoids are thermally degraded.

While pyrolysis is preferred in one embodiment, it is not always necessary to facilitate the recovery, isolation or purification of diamondoids. Other separation methods may allow for the concentration of diamondoids to be sufficiently high given certain feedstocks such that direct purification methods such as chromatography including preparative gas chromatography and high performance liquid chromatography, crystallization, fractional sublimation may be used to isolate diamondoids.

Even after distillation or pyrolysis/distillation, further purification of the material may be desired to provide selected diamondoids for use in the compositions employed in this invention. Such purification techniques include chromatography, crystallization, thermal diffusion techniques, zone refining, progressive recrystallization, size separation, and the like. For instance, in one process, the recovered feedstock is subjected to the following additional procedures: 1) gravity column chromatography using silver nitrate impregnated silica gel; 2) two-column preparative capillary gas chromatography to isolate diamondoids; 3) crystallization to provide crystals of the highly concentrated diamondoids.

An alternative process is to use single or multiple column liquid chromatography, including high performance liquid chromatography, to isolate the diamondoids of interest. As above, multiple columns with different selectivities may be used. Further processing using these methods allow for more refined separations which can lead to a substantially pure component.

Detailed methods for processing feedstocks to obtain higher diamondoid compositions are set forth in U.S. Provisional Patent Application No. 60/262,842 filed Jan. 19, 2001; U.S. Provisional Patent Application No. 60/300,148 filed Jun. 21, 2001; and U.S. Provisional Patent Application No. 60/307,063 filed Jul. 20, 2001, and a co-pending application titled "Processes for concentrating higher diamondoids," by B. Carlson et al., assigned to the assignee of the present application. These applications are herein incorporated by reference in their entirety.

Synthesis of Heterodiamondoids

Prior to attempting an actual synthesis, it is often advantageous to utilize the methods of molecular modeling and computational chemistry in order to predict the properties of a desired molecule, and to facilitate the design of a synthetic pathway. These methods calculate the potential energy surface of a molecule, which takes into account the forces of interaction between the constituent atoms. The methods may be used to predict the three-dimensional arrangement of atoms that correspond to a minimum in the energy of interaction (indicating a stable geometrical configuration), and other properties such as the heat of formation (indicating the difficulty in creating that particular arrangement). Such software programs are commercially available, and include programs such as CS Chem3D Ultra Molecular Modeling and Analysis, available from CambridgeSoft, Cambridge, Mass.

Computational methods fall into two broad categories: 1) those that apply the laws of classical physics to the atomic nuclei of the molecule, a discipline referred to as molecular mechanics, and 2) those that rely on quantum mechanics (i.e. Schrodinger's equation) to describe the electronic structure of the molecule. Quantum mechanical methods include semiempirical methods. In the following analysis, the "MM2 Force Field" method of CS Chem 3D was utilized, which is a molecular mechanical method, as well as the "MOPAC" function that features semi-empirical methods such as AM1, MNDO/3, MNDO, and PM3.

Briefly, to minimize the potential energy surface of the molecule under consideration using the MM2 method the following two steps are performed: first, a model of the molecule is constructed, and second, the convergence criteria for the gradient of the potential energy surface are set. A default value of 0.100 is a reasonable compromise between accuracy and speed; in the following analysis, a value of 0.0100 and the default value were evaluated and compared. The minimized energy and the heat of formation in the MM2 and AM1 computations are the gas-phase values; all other parameters used in the computations were default parameters supplied by the software.

Figure 4A:
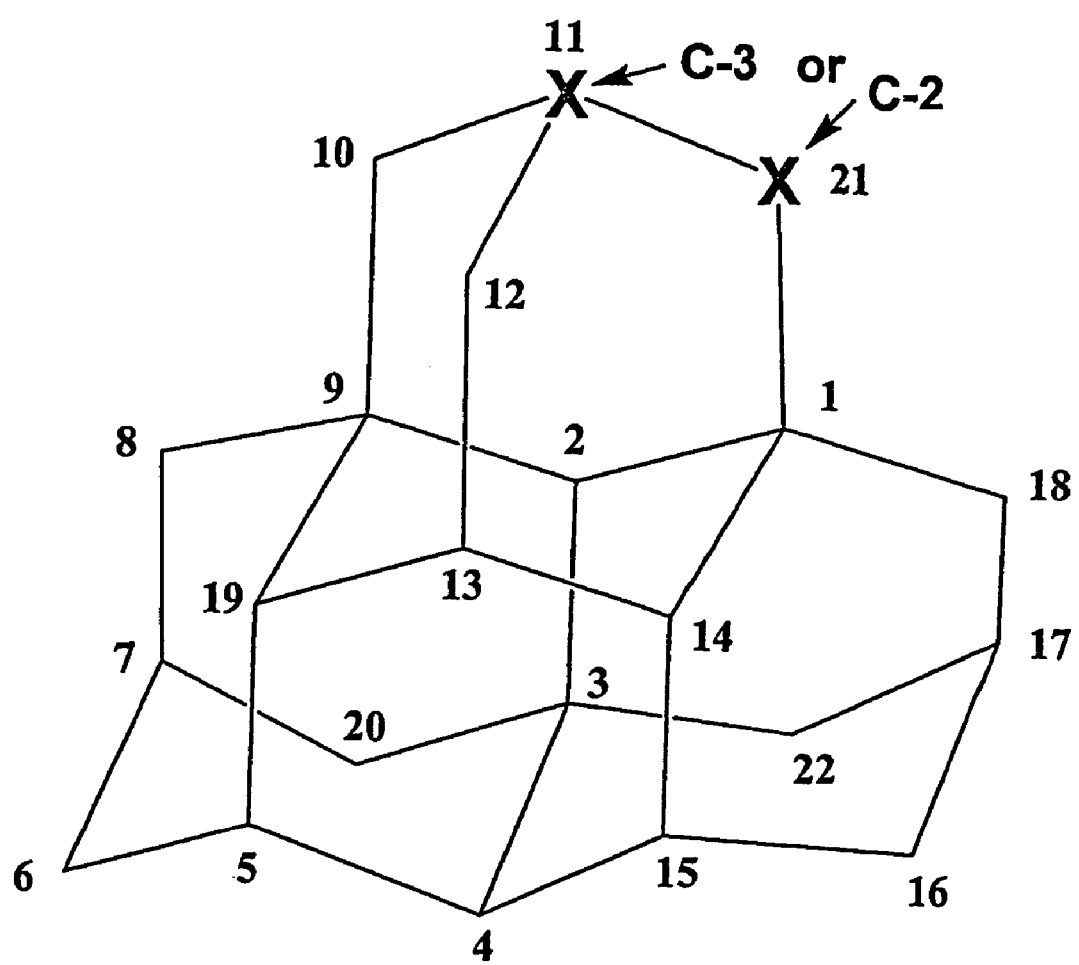
FIGS. 4A-4C present exemplary computer modelling calculations the illustrate the stability of a heterodiamondoid.
Figure 4B:
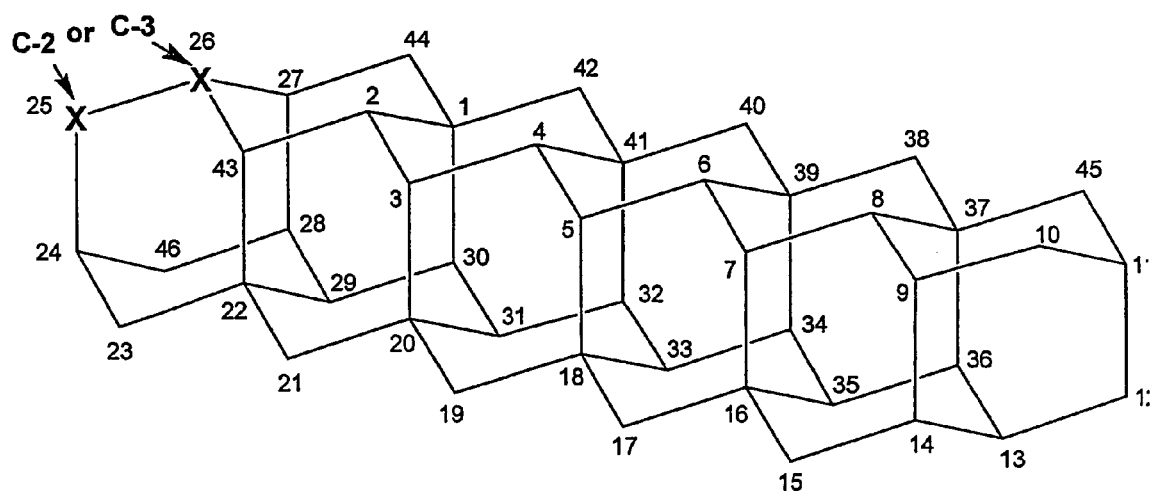

The results of an exemplary calculation for the diamondoid the hetero-iso-tetramantane are provided in Table I and FIG. 4A. After optimizing the molecular structure and calculating the minimized energy, the heat of formation was calculated (it is necessary to compute the minimized energy first, since this result is used in the calculation for the heat of formation). In the Table I and FIG. 4A, "X" represents a heteroatom (where "heteroatom" means an atom of an element other than carbon) that has been inserted into the diamond lattice substitutionally. The second column of the table denotes the position where the heteroatom replaces a host carbon atom, and these positons are either denoted "C-2" for secondary positions, or "C-3" for tertiary positions. The third column of the table tabulates is the heat of formation in kcal/mol. Although the heterodiamondoids of the present invention contain the heteroatoms at substantially substitutional sites, in some embodiments the impurity heteroatoms may be present in interstitial sites. In one embodiment, the heterodiamondoid is substantially free of heteroatoms. In another embodiment, no more than about 20 percent by number of the heteroatoms are present in interstitial sites. In a preferred embodiment, no more than about 10 percent by number of the heteroatoms are present in interstitial sites. In an even more preferred embodiment, no more than about 5 percent of the heteroatoms are present in interstitial sites.

TABLE I

| Heteroatom (X) | Position | Heat of formation (kcal/mol) |
| --- | --- | --- |
| C |  | −52.75 |
| B | C-2 | −18.40 |
|  | C-3 | −9.32 |
| N | C-2 | −34.28 |
|  | C-3 | −26.94 |
| P | C-2 | −16.19 |
|  | C-3 | −15.85 |
| As | C-2 | −20.68 |
|  | C-3 | −18.63 |

Although molecular modelling programs differ in accuracy and focus, and no particular emphasis was placed on accuracy in the calculations of Table I, the present calculations do serve to demonstrate that the heat of formation value of any of the heterodiamondoids shown in the table is roughly the same as the parent diamondoid precursor. This means that the heterodiamondoids shown above exist in configurations that are as stable, or almost as stable, as their parent compounds. Therefore the preparation of such compounds is synthetically feasible.

A similar set of calculations may be made for the hetero-[121212121] decamantane, with the results shown in Table II:

TABLE II

| Heteroatom (X) | Position | Heat of formation (Kcal/mol) |
| --- | --- | --- |
| C |  | −76.08 |
| B | C-2 | −42.40 |
|  | C-3 | −31.76 |
| N | C-2 | −56.91 |
|  | C-3 | −48.15 |
| P | C-2 | −28.44 |
|  | C-3 | −27.10 |

TABLE II-continued

| Heteroatom (X) | Position | Heat of formation (Kcal/mol) |
| --- | --- | --- |
| As | C-2 | −43.59 |
|  | C-3 | −44.52 |

Again, the heats of formation of these heterodiamonds indicate that a synthesis is feasible.

Figure 4C:
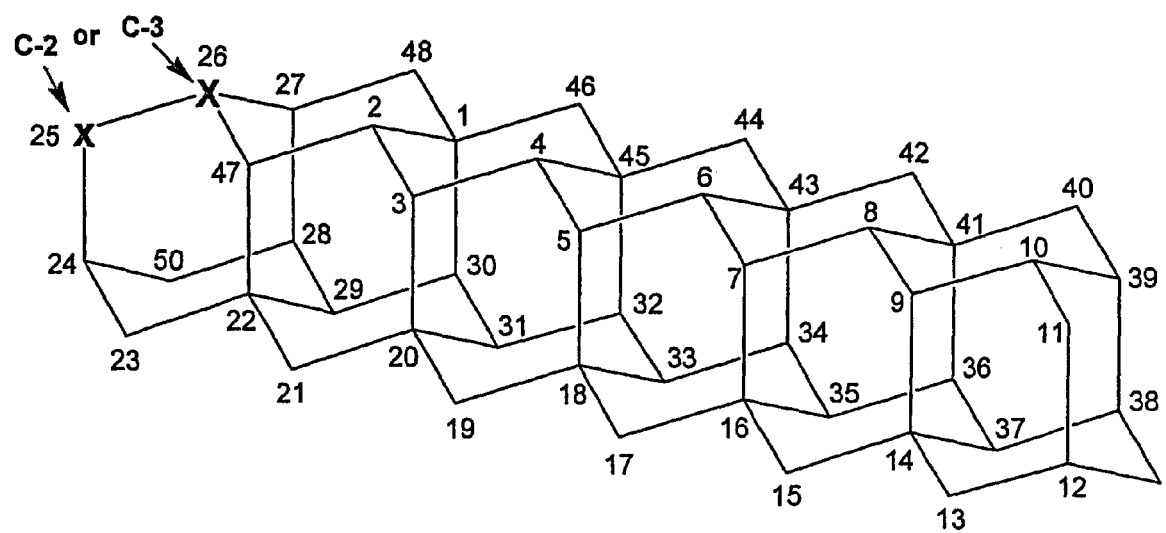

A final example of a caclucation is presented for hetero-[1212121212] undecamantane. For this particular isomer, the results of the calculations are shown in Table III. In this example, the substitution is made at either the secondary C-2 atom at position 25, or the tertiary position at 26. The results of the calculation are shown in FIG. 4C and Table III:

TABLE III

| Heteroatom (X) | Position | Heat of formation (Kcal/mol) |
| --- | --- | --- |
| C |  | −79.81 |
| B | C-2 | −45.45 |
|  | C-3 | −35.85 |
| N | C-2 | −60.32 |
|  | C-3 | −52.45 |
| P | C-2 | −32.05 |
|  | C-3 | −29.80 |
| As | C-2 | −47.70 |
|  | C-3 | −47.96 |

Once again, the heat of formation of the boron, nitrogen, and phosphorus-containing heterodiamondoids are similar to their all-carbon precursors, indicating that the synthesis is feasible.

Thus, molecular modeling calculations have demonstrated that it is feasible to substitutionally position a boron, nitrogen, phosphorus, or arsenic heteroatom into the diamond lattice of a diamondoid. Next, the actual synthesis of such heterodiamondoids will be discussed. Although some heteroadamantane and heterodiamantane compounds have been synthesized in the past, and this may suggest a starting point for the synthesis of heterodiamondoids having more than two or three fused adamantane subunits, it will be appreciated by those skilled in the art that the complexity of the individual reactions and overall synthetic pathways increase as the number of adamantane subunits increases. For example, it may be necessary to employ protecting groups, or it may become more difficult to solubilize the reactants, or the reaction conditions may be vastly different from those that would have been used for the analagous reaction with adamantane. Nevertheless, it can be advantageous to discuss the chemistry underlying heterodiamondoid synthesis using adamantane or diamantane as a substrate because to the intentors' knowledge these are the only systems for which data has been available, prior to the present application.

Nitrogen hetero-adamantane compounds have been synthesized in the past. For example, in an article by T. Sasaki et al., "Synthesis of adamantane derivatives. 39. Synthesis and acidolysis of 2-azidoadamantanes. A facile route to 4-azahomoadamant-4-enes," *Heterocycles*, Vol. 7, No. 1, p. 315 (1977). These authors reported a synthesis of 1-azidoadamantane and 3-hydroxy-4-azahomoadamantane from 1-hydroxyadamantane. The procedure consisted of a substitution of a hydroxyl group with an azide function via the formation of a carbocation, followed by acidolysis of the azide product.

In a related synthetic pathway, Sasaki et al. were able to subject an adamantanone to the conditions of a Schmidt reaction, producing a 4-keto-3-azahomoadamantane as a rearranged product. For details pertaining to the Schmidt reaction, see T. Sasaki et al., "Synthesis of Adamantane Derivatives. XII. The Schmidt Reaction of Adamantane-2-one," *J. Org. Chem.*, Vol. 35, No. 12, p. 4109 (1970).

Alternatively, an 1-hydroxy-2-azaadamantane may be synthesized from 1,3-dibromoadamantane, as reported by A. Gagneux et al. in "1-Substituted 2-heteroadamantanes," *Tetrahedron Letters* No. 17, pp. 1365-1368 (1969). This was a multiple-step process, wherein first the di-bromo starting material was heated to a methyl ketone, which subsequently underwent ozonization to a diketone. The diketone was heated with four equivalents of hydroxylamine to produce a 1:1 mixture of cis and trans-dioximes; this mixture was hydrogenated to the compound 1-amino-2-azaadamantane dihydrochloride. Finally, nitrous acid transformed the dihydrochloride to the hetero-adamantane 1-hydroxy-2-azadamantane.

Alternatively, a 2-azaadamantane compound may be synthesized from a bicyclo[3.3.1]nonane-3,7-dione, as reported by J. G. Henkel and W. C. Faith, in "Neighboring group effects in the β-halo amines. Synthesis and solvolytic reactivity of the anti-4-substituted 2-azaadamantyl system," in *J. Org. Chem.* Vol. 46, No. 24, pp. 4953-4959 (1981). The dione may be converted by reductive amination (although the use of ammonium acetate and sodium cyanoborohydride produced better yields) to an intermediate, which may be converted to another intermediate using thionyl choloride. Dehalogenation of this second intermediate to 2-azaadamantane was accomplished in good yield using $LiAlH_4$ in DME.

A synthetic pathway that is related in principal to one used in the present invention was reported by S. Eguchi et al. in "A novel route to the 2-aza-adamantyl system via photochemical ring contraction of epoxy 4-azahomoadamantanes," *J. Chem. Soc. Chem. Commun.*, p. 1147 (1984). In this approach, a 2-hydroxyadamantane was reacted with a $NaN_3$ based reagent system to form the azahomoadamantane, with was then oxidized by m-chloroperbenzoid acid (m-CPBA) to give an epoxy 4-azahomoadamantane. The epoxy was then irradiated in a photochemical ring contraction reaction to yield the N-acyl-2-aza-adamantane.

Figure 5A:
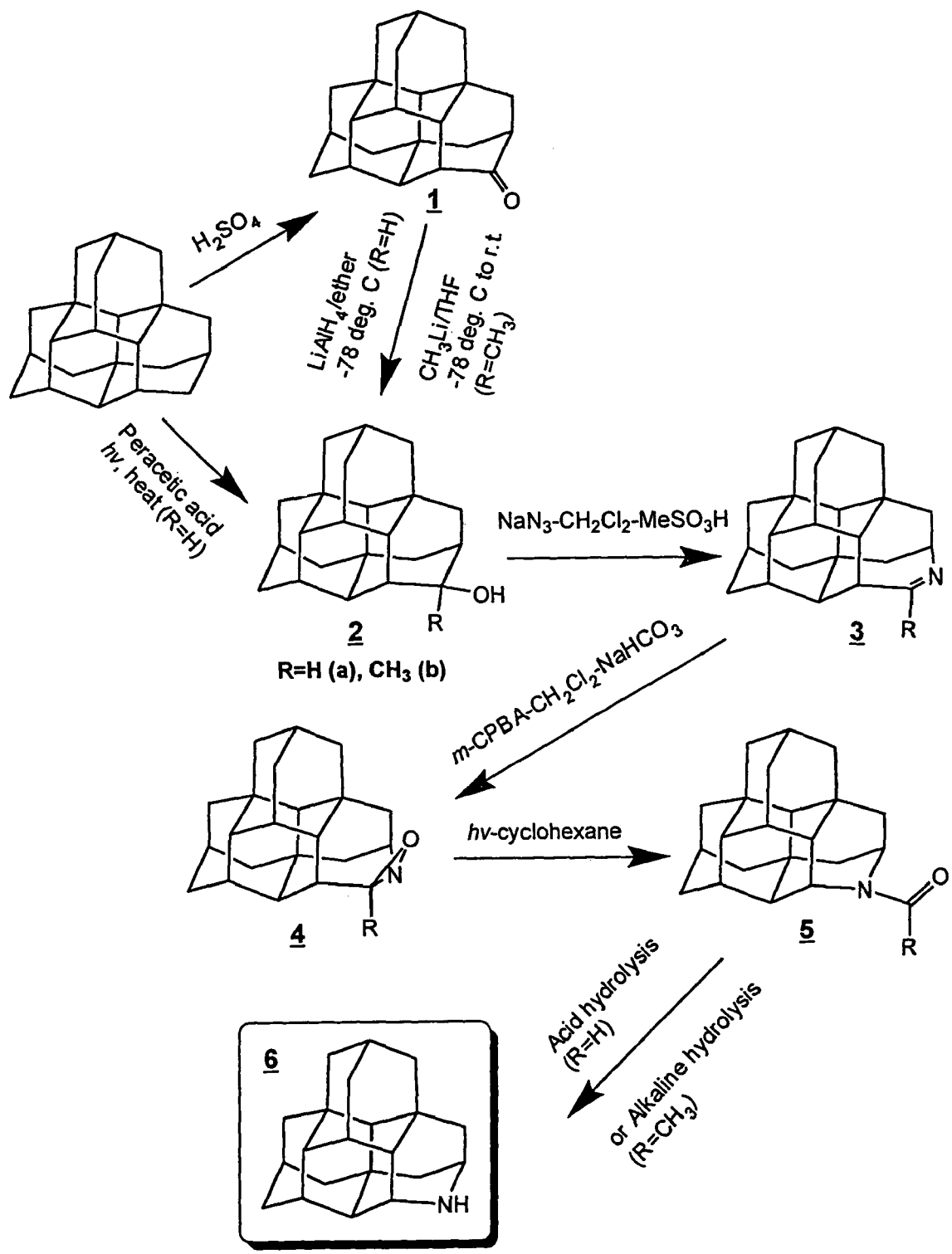
FIGS. 5A-5B illustrate exemplary pathways for synthetically producing heterodiamondoids.
Figure 5B:
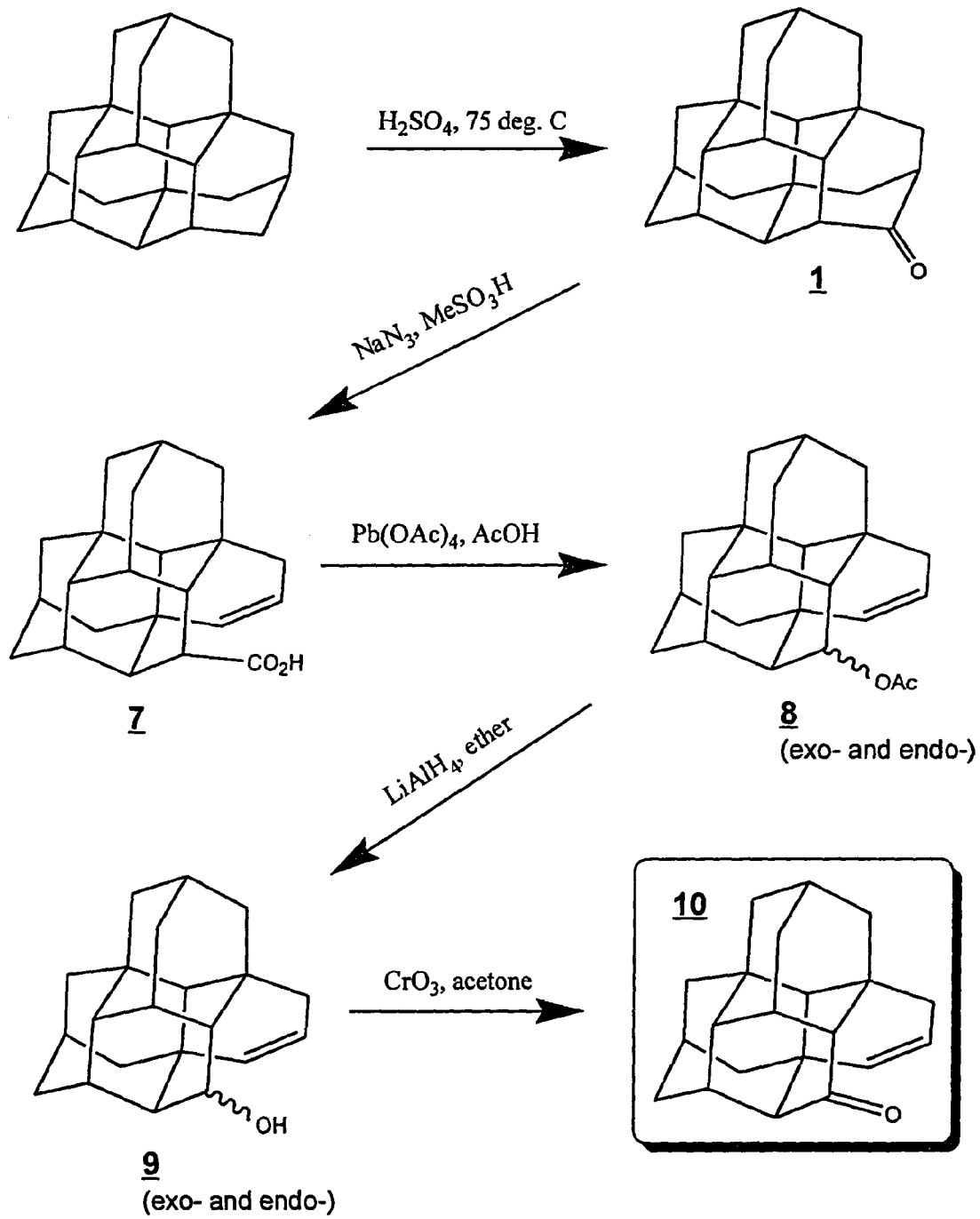

An exemplary reaction pathway for synthesizing a nitrogen containing hetero iso-tetramantane is illustrated in FIG. 5A. It will be known to those of ordinary skill in the art that the reactions conditions of the pathway depicted in FIG. 5A will be substantially different from those of Eguchi due to the differences in size, solubility, and reactivities of tetramantane in relation to adamantane. A second pathway available for synthesizing nitrogen containing heterodiamondoids is illustrated in FIG. 5B.

In another embodiment of the present invention, a phosphorus containing heterodiamondoid may be synthesized by adapting the pathway outlined by J. J. Meeuwissen et. al in "Synthesis of 1-phosphaadamantane," *Tetrahedron* Vol. 39, No. 24, pp. 4225-4228 (1983). It is contemplated that such a pathway may be able to synthesis heterodiamondoids that contain both nitrogen and phosphorus atoms substitutionally positioned in the diamondoid structure, with the advantages of having two different types of electron donating heteroatoms in the same structure.

After preparing heterodiamondoids from diamondoids having no impurity atoms, the resulting heterodiamondoids may be fabricated into bulk materials for use in semiconductor devices. Alternatively, it is contemplated that the heterodiamondoids may be used at a molecular level, where bulk materials are not necessary. The preparation of these materials will be discussed next, and they are also discussed in a copending application titled "Heterodiamondoids," by S. Liu, J. E. Daho, and R. M. Carlson, assigned to the assignee of the present application, and incorporated herein in its entirety.

Preparation of n and p-type Heterodiamondoid Materials

An overview of exemplary methods for fabricating n and p-type materials from heterodiamondoid molecules was shown in FIG. 1. These methods included CVD techniques, polymerization techniques, crystallized aggregates, and use of the diamondoids at the molecular level. The term "materials preparation" as used herein refers to processes that take the heterodiamondoids after they have been synthesized from diamondoid feedstocks, and fabricates them into n and p-type diamondoid-containing materials. In a first embodiment, heterodiamondoids are injected into a reactor carrying out a conventional CVD process such that the heterodiamondoids are added to and become a part of an extended diamond structure, and the heteroatom, being substitutionally positioned on a diamond lattice site, behaves like a dopant in conventionally produced doped diamond. In a second embodiment, the heterodiamondoids may be derivatized (or functionalized) with functional groups capable of polymerizing, and in one embodiment, the functional groups linking two adjacent heterodiamondoids are electrically semiconducting. In a third embodiment, the n or p-type material comprises only heterodiamondoids in a bulk heterodiamondoid crystal, wherein the individual heterodiamondoids in the crystal are held together by Van der waals (London) forces. Finally, in a fourth embodiment, a single heterodiamondoid is used in a nanodevice such as a single electron transistor.

In a first embodiment, n and p-type diamondoid materials are fabricated according to embodiments of the present invention using chemical vapor deposition (CVD) techniques. Heterodiamondoids may be employed as carbon precursors and as self-contained dopant sources already $sp^3$-hybridized in a diamond lattice, using conventional CVD techniques. In a novel approach, the use of the heterodiamondoids may be used to nucleate a diamond film using conventional CVD techniques, where such conventional techniques include thermal CVD, laser CVD, plasma-enhanced or plasma-assisted CVD, electron beam CVD, and the like.

Conventional methods of synthesizing diamond by plasma enhanced chemical vapor deposition (PECVD) techniques are well known in the art, and date back to around the early 1980's. Although it is not necessary to discuss the specifics of these methods as they relate to the present invention, one point in particular that should be made since it is relevant to the role hydrogen plays in the synthesis of diamond by "conventional" plasma-CVD techniques.

In one method of synthesizing diamond films discussed by A. Erdemir et al. in "Tribology of Diamond, Diamond-Like Carbon, and Related Films," in *Modern Tribology Handbook*, Vol. Two, B. Bhushan, Ed. (CRC Press, Boca Raton, 2001) pp. 871-908, a modified microwave CVD reactor is used to deposit a nanocrystalline diamond film using a $C_{60}$ fullerene, or methane, gas carbon precursor. To introduce the $C_{60}$ fullerene precursor into the reactor, a device called a "quartz transpirator" is attached to the reactor, wherein this device essentially heats a fullerene-rich soot to temperatures between about 550 and 600° C. to sublime the $C_{60}$ fullerene into the gas phase.

Figure 6:
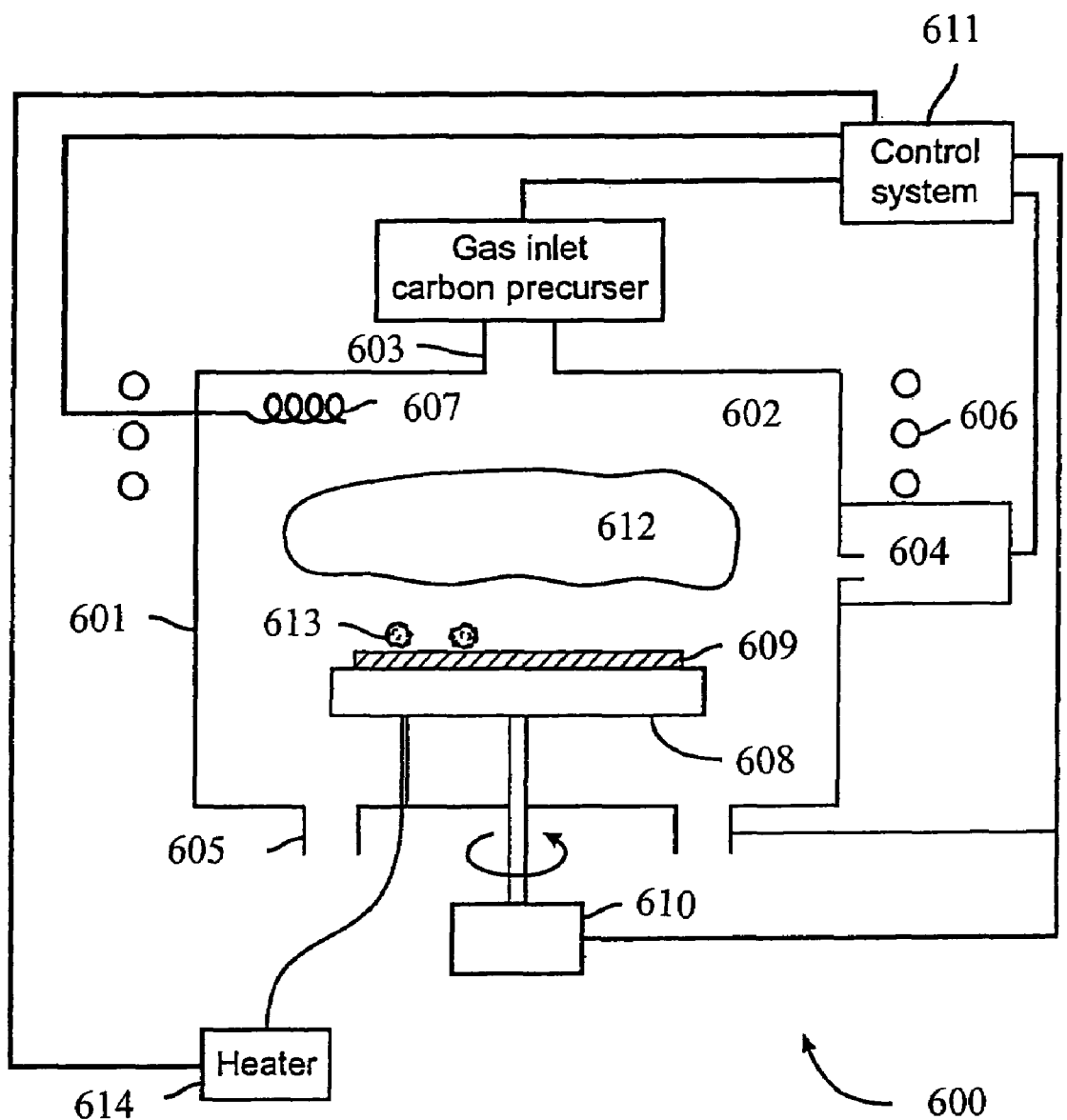
FIG. 6 illustrates an exemplary processing reactor in which an n or p-type heterodiamondoid material may be made using chemical vapor deposition (CVD) techniques.

It is contemplated that a similar device may be used to sublime heterodiamondoids into the gas phase such that they may be introduced to a CVD reactor. An exemplary reactor is shown in generally at 600 in FIG. 6. A reactor 600 comprises reactor walls 601 enclosing a process space 602. A gas inlet tube 603 is used to introduce process gas into the process space 602, the process gas comprising methane, hydrogen, and optionally an inert gas such as argon. A diamondoid subliming or volatilizing device 604, similar to the quartz transpirator discussed above, may be used to volatilize and inject a diamondoid containing gas into the reactor 600. The volatilizer 604 may include a means for introducing a carrier gas such as hydrogen, nitrogen, argon, or an inert gas such as a noble gas other than argon, and it may contain other carbon precursor gases such as methane, ethane, or ethylene.

Consistent with conventional CVD reactors, the reactor 600 may have exhaust outlets 605 for removing process gases from the process space 602; an energy source for coupling energy into process space 602 (and striking a plasma from) process gases contained within process space 602; a filament 607 for converting molecular hydrogen to monoatomic hydrogen; a susceptor 608 onto which a diamondoid containing film 609 is grown; a means 610 for rotating the susceptor 608 for enhancing the $sp^3$-hybridized uniformity of the diamondoid-containing film 609; and a control system 611 for regulating and controlling the flow of gases through inlet 603; the amount of power coupled from source 606 into the processing space 602; the amount of diamondoids injected into the processing space 602; the amount of process gases exhausted through exhaust ports 405; the atomization of hydrogen from filament 607; and the means 610 for rotating the susceptor 608. In an exemplary embodiment, the plasma energy source 606 comprises an induction coil such that power is coupled into process gases within processing space 602 to create a plasma 612.

A heterodiamondoid precursor may be injected into reactor 600 according to embodiments of the present invention through the volatilizer 604, which serves to volatilize the diamondoids. A carrier gas such as methane or argon may be used to facilitate transfer of the diamondoids entrained in the carrier gas into the process space 602. The injection of such heterodiamondoids provides a method whereby impurity atoms may be inserted into a diamond film without having to resort to crystal damaging techniques such as ion implantation.

It is contemplated in some embodiments that the injected methane gas provides the majority of the carbon material present in a CVD created film, with the heterodiamondoid portion of the input gas facilitating the rate of growth, but more importantly, supplying the heteroatom impurity that will eventually function as the electron donor or acceptor in the n and p-type diamond film. This process is illustrated schematically in FIGS. 7A-7C.

Figure 7A:
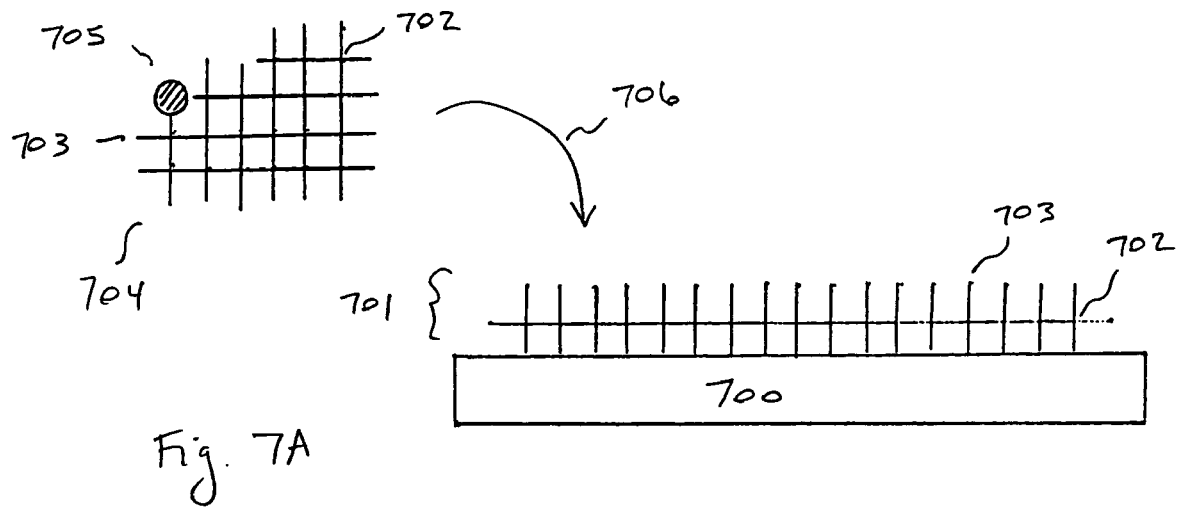
FIGS. 7A-7C illustrate an exemplary process whereby a heterodiamondoid may be used to introduce dopant impurity atoms into a growing diamond film.

Referring to FIG. 7A, a substrate 700 is positioned within the CVD reactor 600, and a conventional CVD diamond film 701 is grown on the substrate 700. This diamond film 701 comprises tetrahedrally bonded carbon atoms, where a carbon atom is represented by the intersection of two lines in FIGS. 7A-C, such as depicted by reference numeral 702, and a hydrogen terminated surface represented by the end of a line, as shown by reference numeral 703. The hydrogen passivated surface 703 of the diamond film 701 is very important. Hydrogen participates in the synthesis of diamond by PECVD techniques by stabilizing the sp bond character of the growing diamond surface. As discussed in the reference cited above, A. Erdemir et al. teach that hydrogen also controls the size of the initial nuclei, dissolution of carbon and generation of condensable carbon radicals in the gas phase, abstraction of hydrogen from hydrocarbons attached to the surface of the growing diamond film, production of vacant sites where $sp^3$ bonded carbon precursors may be inserted. Hydrogen etches most of the double or $sp^2$ bonded carbon from the surface of the growing diamond film, and thus hinders the formation of graphitic and/or amorphous carbon. Hydrogen also etches away smaller diamond grains and suppresses nucleation. Consequently, CVD grown diamond films with sufficient hydrogen present leads to diamond coatings having primarily large grains with highly faceted surfaces.

Referring again to FIG. 7A, a heterodiamondoid 704 is injected in the gas phase into the CVD reactor via the volatilizing device 604 described above. Schematically, the heterodiamondoid 704 has tetrahedrally bonded carbon atoms at the intersections of lines 702, as well as a hydrogen passivated surface at the end of the lines 703, as before. The heterodiamondoid 704 also has a heteroatom 705 substitutionally positioned within its lattice structure, and the heteroatom may be an electron donor or acceptor.

Figure 7B:
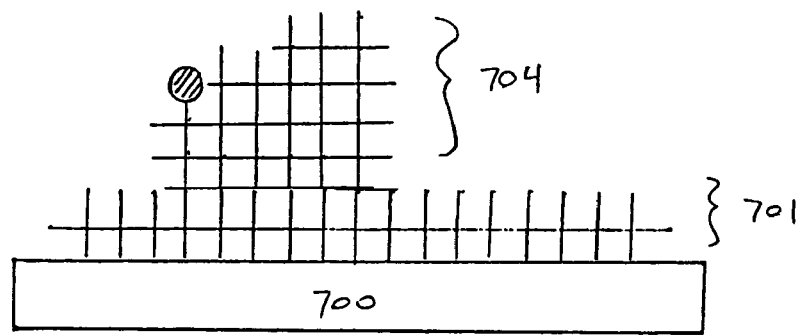

During the deposition process, the heterodiamondoid 704 is deposited on the surface of the CVD diamond film 701, as shown in FIG. 7B. The carbon atoms of the heterodiamondoid 704 become tetrahedrally coordinated with (bonded to) the carbon atoms of the film 701 to produce a continuous diamond lattice structure across the newly created interface of the heterodiamondoid 704 and the diamond film 701.

Figure 7C:
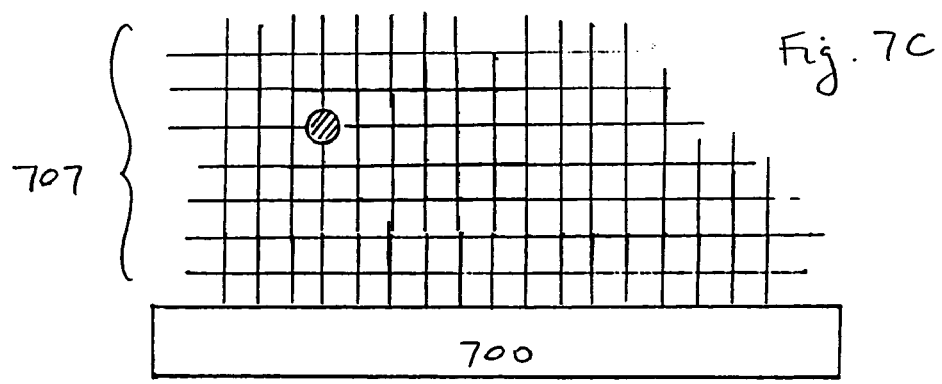

The result is a diamond film 707 having an impurity atom (which may be an electron donor or acceptor) substitutionally positioned on a lattice site position within the diamond crystal structure, as shown in FIG. 7C. Since the heterodiamondoid has been incorporated into the growing diamond film, so has its heteroatom become incorporated into the growing film, and the heteroatom has retained its $sp^3$-hybridization characteristics through the deposition process. Advantages of the present embodiment include the insertion of an impurity atom into the diamond lattice without having to resort to crystal damaging implantation techniques.

The weight of heterodiamondoids and substituted heterodiamondoids, as a function of the total weight of the CVD film (where the weight of the heterodiamondoid functional groups are included in the heterodiamondoid portion), may in one embodiment range from about 1 part per million (ppm) to 10 percent by weight. In another embodiment, the content of heterodiamondoids and substituted heterodiamondoids is about 10 ppm to 1 percent by weight. In another embodiment, the proportion of heterodiamondoids and substituted heterodiamondoids in the CVD film relative to the total weight of the film is about 100 ppm to 0.01 percent by weight.

In an alternative embodiment, heterodiamondoids may be assembled into n and p-type materials by polymerization. For this to occur, it is necessary to derivatize (or functionalize) the heterodiamondoids prior to polymerization, and methods of forming diamondoid derivatives, and techniques for polymerizing derivatized diamondoids, are discussed in U.S. patent application Ser. No. 60/334,939, entitled "Polymerizable Higher Diamondoid Derivatives," by Shenggao Liu, Jeremy E. Dahl, and Robert M. Carlson, filed Dec. 4, 2001, and incorporated herein by reference in its entirety.

To fabricate a polymeric film containing heterodiamondoid constituents, either as part of the main polymeric chain, or as side groups or branches off of the main chain, one first synthesizes a derivatized heterodiamondoid molecule, that is to say, a heterodiamondoid having at least one functional group substituting one of the original hydrogens. As discussed in that application, there are two major reaction sequences that may be used to derivatize heterodiamondoids: nucleophilic ($S_N1$-type) and electrophilic ($S_E2$-type) substitution reactions.

$S_N1$-type reactions involve the generation of heterodiamondoid carbocations, which subsequently react with various nucleophiles. Since tertiary (bridgehead) carbons of heterodiamondoids are considerably more reactive than secondary carbons under $S_N1$ reaction conditions, substitution at a tertiary carbon is favored.

$S_E2$-type reactions involve an electrophilic substitution of a C—H bond via a five-coordinate carbocation intermediate. Of the two major reaction pathways that may be used for the functionalization of heterodiamondoids, the $S_N1$-type may be more widely utilized for generating a variety of heterodiamondoid derivatives. Mono and multi-brominated heterodiamondoids are some of the most versatile intermediates for functionalizing heterodiamondoids. These intermediates are used in, for example, the Koch-Haaf, Ritter, and Friedel-Crafts alkylation and arylation reactions. Although direct bromination of heterodiamondoids is favored at bridgehead (tertiary) carbons, brominated derivatives may be substituted at secondary carbons as well. For the latter case, when synthesis is generally desired at secondary carbons, a free radical scheme is often employed.

Although the reaction pathways described above may be preferred in some embodiments of the present invention, many other reaction pathways may certainly be used as well to functionalize a heterodiamondoid. These reaction sequences may be used to produce derivatized heterodiamondoids having a variety of functional groups, such that the derivatives may include heterodiamondoids that are halogenated with elements other than bromine (e.g. fluorine), alkylated diamondoids, nitrated diamondoids, hydroxylated diamondoids, carboxylated diamondoids, ethenylated diamondoids, and aminated diamondoids. See Table 2 of the co-pending application "Polymerizable Higher Diamondoid Derivatives" for a listing of exemplary substituents that may be attached to heterodiamondoids.

Heterodiamondoids, as well as heterodiamondoid derivatives having substituents capable of entering into polymerizable reactions, may be subjected to suitable reaction conditions such that polymers are produced. The polymers may be homopolymers or heteropolymers, and the polymerizable diamondoid and/or heterodiamondoid derivatives may be co-polymerized with nondiamondoid, diamondoid, and/or heterodiamondoid-containing monomers. Polymerization is typically carried out using one of the following methods: free radical polymerization, cationic, or anionic polymerization, and polycondensation. Procedures for inducing free radical, cationic, anionic polymerizations, and polycondensation reactions are well known in the art.

Free radical polymerization may occur spontaneously upon the absorption of an adequate amount of heat, ultraviolet light, or high-energy radiation. Typically, however, this polymerization process is enhanced by small amounts of a free radical initiator, such as peroxides, aza compounds, Lewis acids, and organometallic reagents. Free radical polymerization may use either non-derivatized or derivatized heterodiamondoid monomers. As a result of the polymerization reaction a covalent bond is formed between diamondoid, nondiamondoid, and heterodiamondoid monomers such that the diamondoid or heterodiamondoid becomes part of the main chain of the polymer. In another embodiment, the functional groups comprising substituents on a diamondoid or heterodiamondoid may polymerize such that the diamondoids or heterodiamondids end up being attached to the main chain as side groups. Diamondoids and heterodiamonhdoids having more than one functional group are capable of cross-linking polymeric chains together.

For cationic polymerization, a cationic catalyst may be used to promote the reaction. Suitable catalysts are Lewis acid catalysts, such as boron trifluoride and aluminum trichloride. These polymerization reactions are usually conducted in solution at low-temperature.

In anionic polymerizations, the derivatized diamondoid or heterodiamdondoid monomers are typically subjected to a strong nucleophilic agent. Such nucleophiles include, but are not limited to, Grignard reagents and other organometallic compounds. Anionic polymerizations are often facilitated by the removal of water and oxygen from the reaction medium.

Polycondensation reactions occur when the functional group of one diamondoid or heterodiamondoid couples with the functional group of another; for example, an amine group of one diamondoid or heterodiamondoid reacting with a carboxylic acid group of another, forming an amide linkage. In other words, one diamondoid or heterodiamondoid may condense with another when the functional group of the first is a suitable nucleophile such as an alcohol, amine, or thiol group, and the functional group of the second is a suitable electrophile such as a carboxylic acid or epoxide group. Examples of heterodiamondoid-containing polymers that may be formed via polycondensation reactions include polyesters, polyamides, and polyethers.

In one embodiment of the present invention, a synthesis technique for the polymerization of heterodiamondoids comprises a two-step synthesis. The first step involves an oxidation to form at least one ketone functionality at a secondary carbon (methylene) position of a heterodiamondoid. The heterodiamondoid may be directly oxidized using a reagent such as concentrated sulfuric acid to produce a keto-heterodiamondoid. In other situations, it may be desirable to convert the hydrocarbon to an alcohol, and then to oxidize the alcohol to the desired ketone. Alternatively, the heterodiamondoid may be initially halogenated (for example with N-chlorosuccinimide, NCS), and the resultant halogenated diamondoid reacted with base (for example, $KHCO_3$ or $NaHCO_3$, in the presence of dimethyl sulfoxide). It will be understood by those skilled in the art that it may be necessary to protect the heteroatom in the heterodiamondoid prior to the oxidation step.

The second step consists of the coupling two or more keto-heterodiamondoids to produce the desired polymer of heterodiamondoids. It is known in the art to couple diamondoids by a ketone chemistry, and one process has been described as the McMurry coupling process in U.S. Pat. No. 4,225,734. Alternatively, coupling may be effected by reacting the keto-heterodiamondoids in the presence of $TiCl_3$, Na, and 1,4-dioxane. Additionally, polymers of diamondoids (adamantanes) have been illustrated in Canadian Patent Number 2100654. One of ordinary skill in the art will understand that because of the large number of oxidation and coupling reaction conditions available, a variety of keto-heterodiamondoids may be prepared with a diversity of configurational, positional, and stereo configurations.

In an alternative embodiment, it is desirable to conduct a sequence of oxidation/coupling steps to maximize the yield of a heterodiamondoid polymer. For example, when the desired polymeric heterodiamondoid contains interposing bridgehead carbons, a three step procedure may be useful. This procedure comprises chlorinating an intermediate coupled polymeric heterodiamondoid with a selective reagent such as NCS. This produces a chlorinated derivative with the newly introduced chlorine on a methylene group adjacent to the double bond (or bonds) that were present in the intermediate. The chloro-derivative is convertable to the desired ketone by substitution of the chlorine by a hydroxyl group, and further oxidation by a reagent such as sodium bicarbonate in dimethylsulfoxide (DMSO). Additional oxidation may be carried out to increase ketone yields, the additional treatment comprising further treatment with pyridine chlorochromate (PCC).

Figure 8:
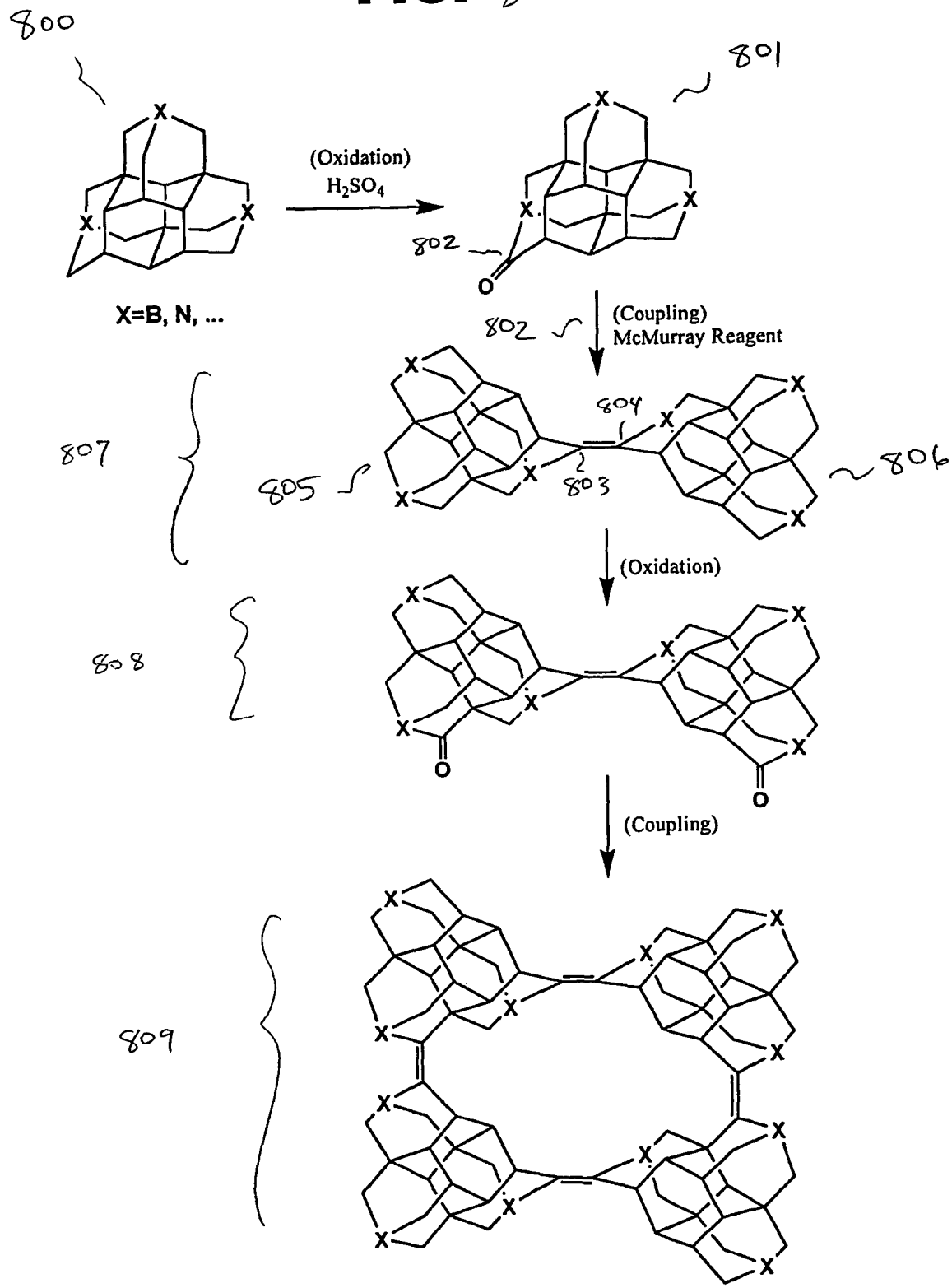
FIG. 8 is an exemplary reaction scheme for the synthesis of a polymer from n-type or p-type heterodiamondoids.

A schematic illustration of a polymerization reaction between heterodiamondoid monomers is illustrated in FIG. 8A. A heterodiamondoid 800 is oxidized using sulfuric acid to the keto-heterodiamondoid 801. The particular diamondoid shown at 801 is a tetramantane, however, any of the diamondoids described above are applicable. Again, the symbol "X" represents a heteroatom substitutionally positioned on a lattice site of the diamondoid. The ketone group in this instance is attached to position 802.

Two heterodiamondoids 801 may be coupled using a McMurry reagent as shown in step 802. According to embodiments of the present invention, the coupling between two adjacent heterodiamondoids may be made between any two carbons of each respective heterodiamondoid's nuclear structure, and in this exemplary situation the coupling has been made between carbons 803 of diamondoid 806 and carbon 804 of heterodiamondoid 806. It will be apparent to those skilled in the art that this process may be continued; for example, the pair of heterodiarnondoids shown generally at 807 may be functionalized with ketone groups on the heterodiamondoids 805 and 806, respectively, to produce the intermediate 808, where two intermediates 808 may couple to form the complex 809. In this manner, a polymer may be constructed using the individual heterodiamondoids 800 such that n-type or p-type material is fabricated. Such a material is expected to be electrically conducting due to the pi-bonding between adjacent heterodiamondoid monomers.

In an alternative embodiment, individual heterodiamondoid molecules may be coupled with electrically conductive polymer "linkers" to generate an n-type or p-type heterodiamondoid material. In this context, a linker is defined as a short segment of polymer comprising one to ten monomer segments of a larger polymer. The linkers of the present invention may comprise a conductive polymer such that electrical conductivity is established between adjacent heterodiamondoids in the overall bulk material. Polymers with conjugated pi-electron backbones are capable of displaying these electronic properties. Conductive polymers are known, and the technology of these materials have been described in a chapter titled "Electrically Conductive Polymers" by J. E. Frommer and R. R. Chance in High Performance Polymers and Composites, J. I. Kroschwitx, Ed. (Wiley, New York, 1991), pp. 174 to 219. The conductivity of many of these polmers have been described in this chapter, and compared to metals, semiconductors, and insulators. A typical semiconducting polymer is poly(p-phenylene sulfide), which has a conductivity as high as $10^3$ Siemens/cm$^2$ (these units are identical to $\Omega^{-1}$ cm$^{-1}$), and as low as $10^{-15}$, which is as insulating as nylon. Polyacetylene is more conducting with an upper conductance of $10^3 \Omega^{-1}$ cm$^{-1}$, and a lower conductance of about $10^{-9} \Omega^{-1}$ cm$^{-1}$.

According to embodiments of the present invention, heterodiamondoids may be electrically connected to form a bulk n or p-type material using oligomers of the polymers discussed above. In this instance, an oligomer refers to a polymerization of about 2 to 20 monomers. Thus, an oligomer may be thought of as a short polymer. In this instance, the purpose of the oligomers, and/or linkers, is to electrically connect a number of heterodiamondoids into a three-dimensional structure such that a bulk material having p-type or n-type electrical conductivity may be achieved.

Conductive polymers have been discussed in general by J. E. Frommer and R. R. Chance in a chapter titled "Electrically conductive polymers," in *High Performance Polymers and Composites*, J. I. Kroschwitz, ed. (Wiley, New York, 1991), pp. 174-219. To synthesize a conventional conductive polymer, it is important to incorporate moieties having an extended pi-electron conjugation. The monomers that are typically used to synthesize such polymers are either aromatic, or contain multiple carbon-carbon double bonds that are preserved the in the final polymeric backbone. Alternatively, conjugation may be achieved in a subsequent step that transforms the innitial polymer product into a conjugated polymer. For example, the polymerization of acetylene yields a product of conjugated ethylene units, whereas a benzene polymerization produces a chain of covalently linked aromatic units.

Figure 9:
FIGS. 9A-9N show exemplary linking groups that are electrically conducting as polymers, and that may be used to link heterodiamondoids to produce n and p-type materials.
Figure 9:
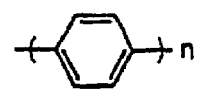
Figure 9:
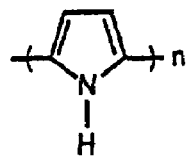
Figure 9:
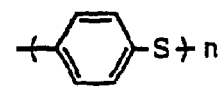
Figure 9:
Figure 9:
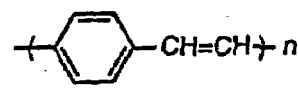
Figure 9:
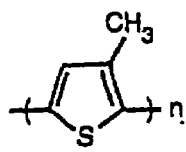
Figure 9:
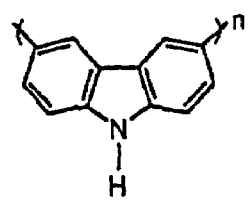
Figure 9:
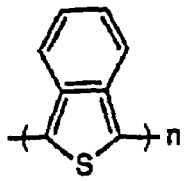
Figure 9:
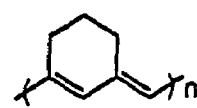

A catalog of exemplary oligomers (linkers) that may be used to connect heterodiamondoids in an electrically conductive manner are illustrated in FIGS. 9A-N. Typical linkers that have been shown to be electrically conductive are polyacetylene in FIG. 9A, polythiophene in FIG. 9E, and polyparaphenylene vinylene in FIG. 9F. An electrically conductive linker that will be highlighted as an example in the next discussion is polyaniline, the oligomer of which has been depicted in FIG. 9N.

Figure 10:
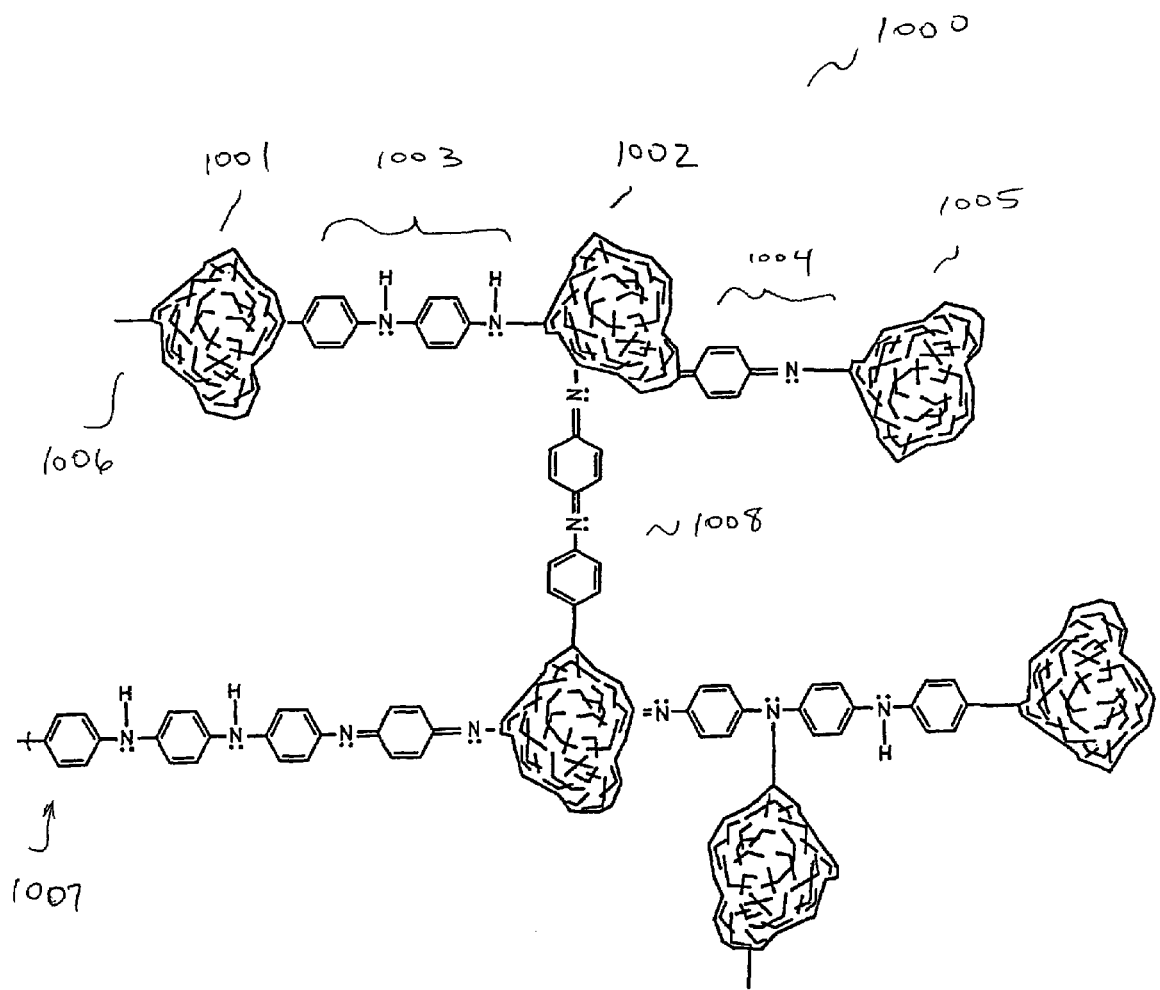
FIG. 10 illustrates an exemplary n or p-type material fabricated from heterodiamondoids linked by polyaniline oligomers.

A schematic diagram of a heterodiamondoid polymer generated with polyaniline linking groups is depicted in FIG. 10. The polymer of FIG. 10 is only exemplary in that the conductive linker groups between adjacent heterodiamondoids is a polyaniline functionality, but of course the linking group could be any conductive polymer, many of which comprise conductive diene systems. In FIG. 10 a heterodiamondoid 1001 is linked to a heterodiamondoid 1002 via a short segment of polyaniline oligomer 1003. The same applies for the connection 1004 to the heterodiamondoid 1005 within the same linear chain.

The polymer shown generally at 1000 may also contain crosslinks that connect a linear chain 1006 with 1007. This creates a three-dimensional crosslinked polymer with electrical conductivity in a three-dimensional sense. Crosslinked chains 1008 may be used to connect adjacent linear chains 1006 and 1007. A three-dimensional matrix of an electrically conducting diamondoid containing material is thus established. Each heterodiamondoid 1001 and 1002 contains within its structure a heteroatom which is either an electrical donor or electrical accepter. Overall, fabrication of an n-type or p-type heterodiamondoid material is achieved.

A third method of fabricating n and p-type materials is crystallize the heterodiamondoids into a solid, where the individual heterodiamondoids comprising the solid are held together by Van der Waals forces (also called London or dispersive forces). Molecules that are held together in such a fashion have been discussed by J. S. Moore and S. Lee in "Crafting Molecular Based Solids," *Chemistry and Industry*, July, 1994, pp. 556-559, and are called "molecular solids" in the art. These authors state that in contrast to extended solids or ionic crystals, the prefered arrangement of molecules in a molecular crystal is presumably one that minimizes total free energy, and thus the fabrication of a molecular crystal is controlled by thermodynamic considerations, unlike a synthetic process. An example of a molecular crystal comprising the pentamantane [1(2,3)4] will be discussed next.

In an exemplary embodiment, a molecular crystal comprising [1 (2,3)4] pentamantane was formed by the chromatographic and crystallographic techniques described above. These aggregations of diamondoids pack to form actual crystals in the sense that a lattice plus a basis may be defined. In this embodiment the [1(2,3)4] pentamantane is found to pack in an orthorhombic crystal system having the space group Pnma, with unit cell dimensions a=11.4786, b=12.6418, and c=12.5169 angstroms, respectively. To obtain that diffraction data, a pentamantane crystal was tested in a Bruker SMART 1000 diffractometer using radiation of wavelength 0.71073 angstroms, the crystal maintained at a temperature of 90 K.

Figure 11:
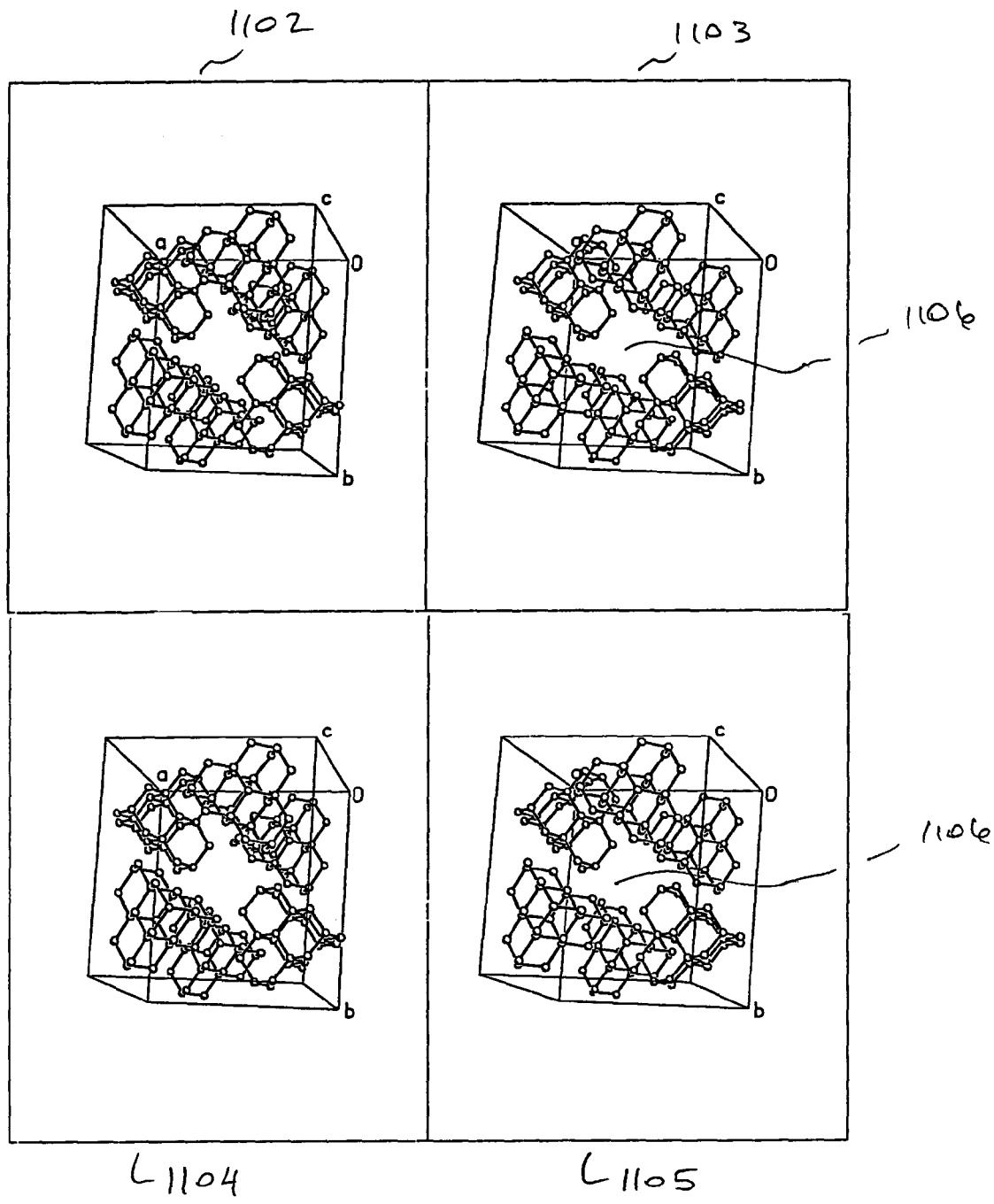
FIG. 11 shows how [1(2,3)4] pentamantane packs to form a crystal aggregate.

A unit cell of the pentamantane molecular crystal is illustrated in FIG. 11. This diagram illustrates the generalized manner in which heterodiamondoids may pack in order to be useful according to embodiments of the present invention. These molecular crystals display well-defined exterior crystal facets, and are transparent to visible radiation.

Referring to FIG. 11, the packing of the [1(2,3)4] pentamantane is illustrated in two dimensions by the unit cells 1102, 1103, 1104, 1104. Each unit cell of the aggregate contains four pentamantane molecules, where the molecules are arranged such that there is one central cavity per unit cell. In some embodiments of the present invention, the cavity 1106 that is created by the packed pentamantane units may accommodate a transition element metal, such as gold, to enhance electrical conductivity.

The significance of the packing of the [1 (2,3)4] pentamantanes illustrated in FIG. 11 is that a p or n-type diamondoid material, and junction fabricated therefrom, may be realized with little further processing than isolation using chromatographic techniques. In other words, no functionalization is necessary to polymerize or link up individual diamondoid molecules, and no expensive deposition equipment is needed in this embodiment. Since these crystal are mechanically soft and easily compressilble, being held together by Van der Waals forces, an exterior "mold" is contemplated to support the various regions of the device (in essence, for example, a transistor may even be "semi-liquid").

In an alternative embodiment, a heterodiamondoid is contemplated to function in a p or n-type capacity at a molecular level, and are contemplated to function as quantum devices such as single electron transistors. Single electron transistors have been discussed in the art. See, for example, U.S. Pat. No. 6,335,245, issued to Park et al., and Quantum Semiconductor Devices and Technologies, T. P Pearsall, ed. (Kluwer, Boston, 2000), pp. 8-12. Park discloses that efforts to reduce device size in the semiconductor industry will drive a reduction in the number of electrons present in a channel (e.g., the conducting pathway between the source and drain of a transistor) from about 300 in the year 2010 to no more than 30 in the year 2020. As the number of electrons necessary for operating a device is reduced, statistical variations in electron behavior will become more of a concern. Thus, although single electron transistors have been conceived, there are a number of difficulties to overcome with regard to their implementation, including the ability to fabricate them using present day lithographic techniques. Pearsall reviews several types of single electron transistors, including metal, semiconducting, carbon nanotube, and superconducting single electron transistors.

An example of a heterodiamondoid contemplated for use in a single electron transistor is shown in FIG. 12. Referring to FIG. 12, an n-type heterodiamondoid comprising a tetramantane 1201 with nitrogen heteroatoms is coupled to a similar tetramantane 1202 through a carbon-carbon double bond 1208 as discussed in the polymer section above. The number of heterodiamondoid molecules in this complex may range from about 1 to 10,000. Similarly, a p-type tetramantane 1203 with boron heteroatoms may be coupled to a similar tetramantane 1204 through a carbon-carbon double bond 1209. On a molecular level, the complex of n-type diamondoids 1205 may be coupled to the complex of p-type diamondoids 1206 to form the complex 1207. Such a molecular complex may function as a single electron transistor.

The heterodiamondoids of the present invention offer enhanced reliability, controllability, and reproducibility not available with prior art methods Devices Fabricated from n and p-type Diamondoid Junctions Electrical devices may be constructed from the n and p-type materials discussed above. Rectifiers (p-n junctions), bipolar junction transistors, and field effect transistors have been discussed by D. R. Askeland in "*The Science and Engineering of Materials*," $2^{nd}$ Ed. (PWS-Kent Publishing, Boston, 1989), pp. 664-667.

In one embodiment of the present invention, a rectifying circuit may be produced by positioning an n-type diamondoid semiconductor material adjacent to a p-type diamondoid semiconductor material to provide a p-n junction. At equilibrium, the n-type diamondoid material contains an excess of electrons relative to the undoped material, and the p-type diamondoid material contains an excess of holes. The electrical imbalance between the electrons in the n-type diamondoid material and the holes in the p-type diamondoid material leads to what is known as a contact potential.

In operation, an external voltage may be applied across the p-n junction. If the negative side of the applied voltage is connected to the n-type side of the junction, and the positive side of the voltage applied to the p-type side, then both electrons and holes will move towards the interface between the n and p-type materials, and the electrons and holes will recombine in the vicinity of the junction. This orientation of the applied voltage is referred to as a forward bias, and the greater the forward bias, the greater the current.

If the orientation of the applied voltage is reversed such that the negative side of the voltage is connected to the p-type side of the junction and the positive side of the voltage is connected to the n-type side of the junction, a reverse biased is created. In this case, both the holes in the p-type material and the electrons in the n-type material move away from the junction. A depletion zone is created in small regions of both the of the p-type and n-type materials adjacent to the junction, where the term "depletion" means that the materials are depleted of their charge carriers in these regions adjacent to the junction. With no charge carriers both materials behave as insulators in the region adjacent to the junction, and little or no current flows across the junction when a reverse bias has been applied.

A p-n junction may be configured to operate as a rectifier because the junction permits current to flow in only one direction; this is the direction where electrons flow out of the n-type side and into the p-type side to recombine with holes (and vice versa), and occurs when a forward bias has been applied. This phenomenon has an application in electronics. The junction passes only one-half of an alternating current waveform, the half in which the negative side of the waveform is applied to the n-type side (forward bias), and in practice converts an alternating current waveform to a direct current waveform. Thus, in this example of the use of heterodiamondoid n and p-type materials in semiconductor devices, the heterodiamondoid p-n junction functions as a rectifier diode.

Diodes make use of a single p-n junction. Most transistors operate on the principal of two adjacent p-n junctions, usually configured as three slabs of material with an orientation of p-n-p or n-p-n. In another embodiment, a transistor may be constructed from two adjacent p-n junctions of heterodiamondoid containing materials. There are essentially two types of transistors: bipolar junction transistors and field effect transistors. Either type may operate as a switch or an amplifier.

Bipolar junction transistors and field effect transistors have been discussed by D. R. Askeland in the above cited reference. Bipolar junction transistors (BJTs) are often used in the central processing units (CPU's) of computers since this type of transistor exhibits a rapid switching response. A bipolar junction transistor is a three-layer sandwich of n and p-type semiconducting materials that alternate between the two types; bipolar transistors (and transistors in general) are typically configured as either n-p-n or p-n-p. The three layers of the sandwich (or zones of the bipolar junction transistor) may be labeled, respectively, the emitter, base, and collector. As in the case of the p-n junction of the diode, electrons are initially concentrated in the n-type material(s) and holes are initially concentrated in the p-type material(s).

Figure 13A:
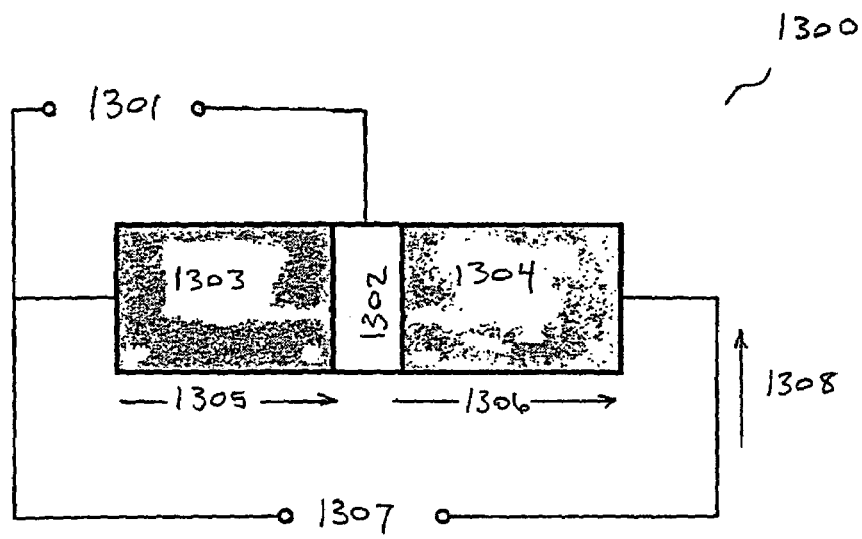
FIGS. 13A-13B are schematic illustrations of an exemplary bipolar transistor fabricated from the present n and p-type heterodiamondoid materials.
Figure 13B:
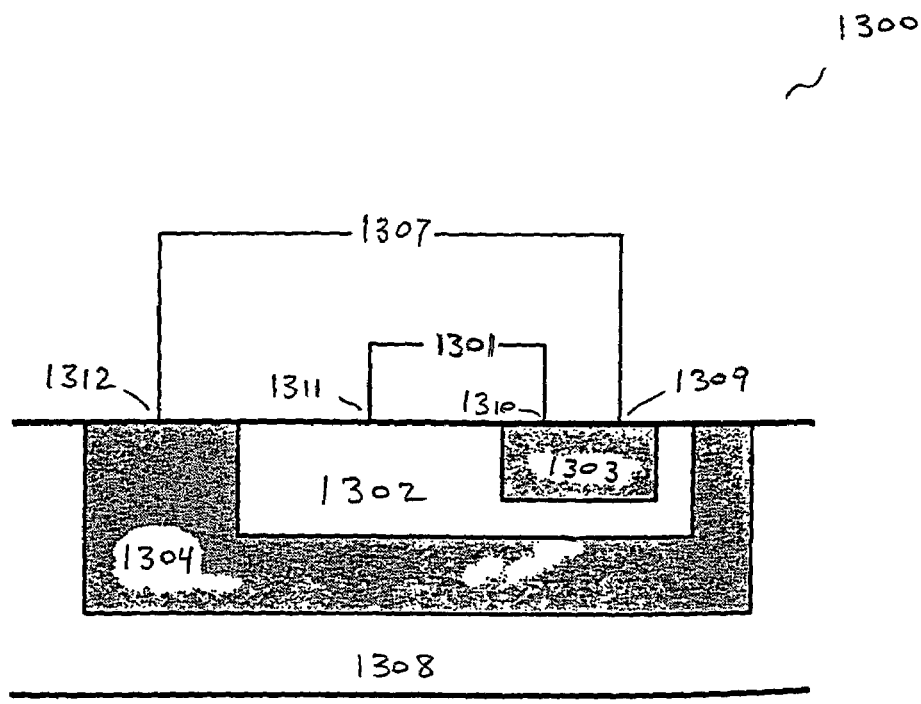

An exemplary n-p-n bipolar transistor that may be fabricated from heterodiamondoid materials, and the equivalent electrical circuit that may be drawn to represent that transistor, is shown in FIGS. 13A-B. The heterodiamondoid-containing bipolar transistor is shown generally at 1300 in FIGS. 13A-B. Referring to FIG. 13A, the electrical signal 1301 to be amplified is connected between the base 1302 (an p-type diamondoid-containing material) and the emitter 1303 (an n-type diamondoid-containing material). The output from the transistor is the voltage between the emitter 1303 and the collector 1304 (also an n-type diamondoid-containing material). The circuit may be connected such that a forward bias 1305 is applied between the emitter 1303 and the base 1302 (this is a forward bias because a negative voltage is being applied to the n-type emitter 1303), and therefore a reverse bias 1306 is generated between the base 1302 and the collector 1304 (this is a reverse bias because a positive voltage is being applied to the n-type collector 1304). The foward bias 1305 causes electrons to leave the emitter 1303 and accelerate into the base 1302.

Operationally, electrons and holes will attempt to recombine in the base 1302, but, as pointed out by Askeland, most of the electrons may be induced to travel through the base 1302 and into the collector 1304 if either the base 1302 is made exceptionally thin, or the recombination time between an electron and a hole in the base 1302 is long. The reverse bias 1306 between the base 1302 and the collector 1304 accelerates the electrons through the collector 1304 such that a circuit is completed and an output signal 1307 is produced. This exemplary bipolar transistor fabricated from heterodiamondoid materials functions in a manner known to those skilled in the art of bipolar transistors: as the input voltage 1301 is increased, a very large current 1308 is produced, and signal amplification has occurred.

A heterodiamondoid-based bipolar transistor as it may appear in the cross-section is shown in FIG. 13B. The bipolar transistor of FIG. 13B is analogous to the electrical circuit shown in FIG. 13A, but the drawing in FIG. 13B is provided to illustrate the appearance of a bipolar transistor as it may actually be fabricated. The device is fabricated on a substrate 1308. An n-type heterodiamondoid well may first be fabricated the becomes the collector 1304. Within this well is fabricated a smaller well of p-type diamondoid material; this well is destined to become the base 1302. Finally, within the base 1302 is fabricated an even smaller well of n-type diamondoid material that becomes the emitter 1303.

In one embodiment of the present invention, it is contemplated that an electrical connection 1309, 1310 may be made to the emitter 1303, an electrical connection 1311 may be made to the base 1302, and an electrical connection 1312 may be made to the collector 1303. The electrical connections 1309, 1310, 1311, 1312 may be made using "molecular wires" such as carbon nanotubes. Methods for making ohmic contacts to diamond are known to those skilled in the art: see, for example, U.S. Pat. No. 5,075,757, issued to Ishii et al.

Figure 14:
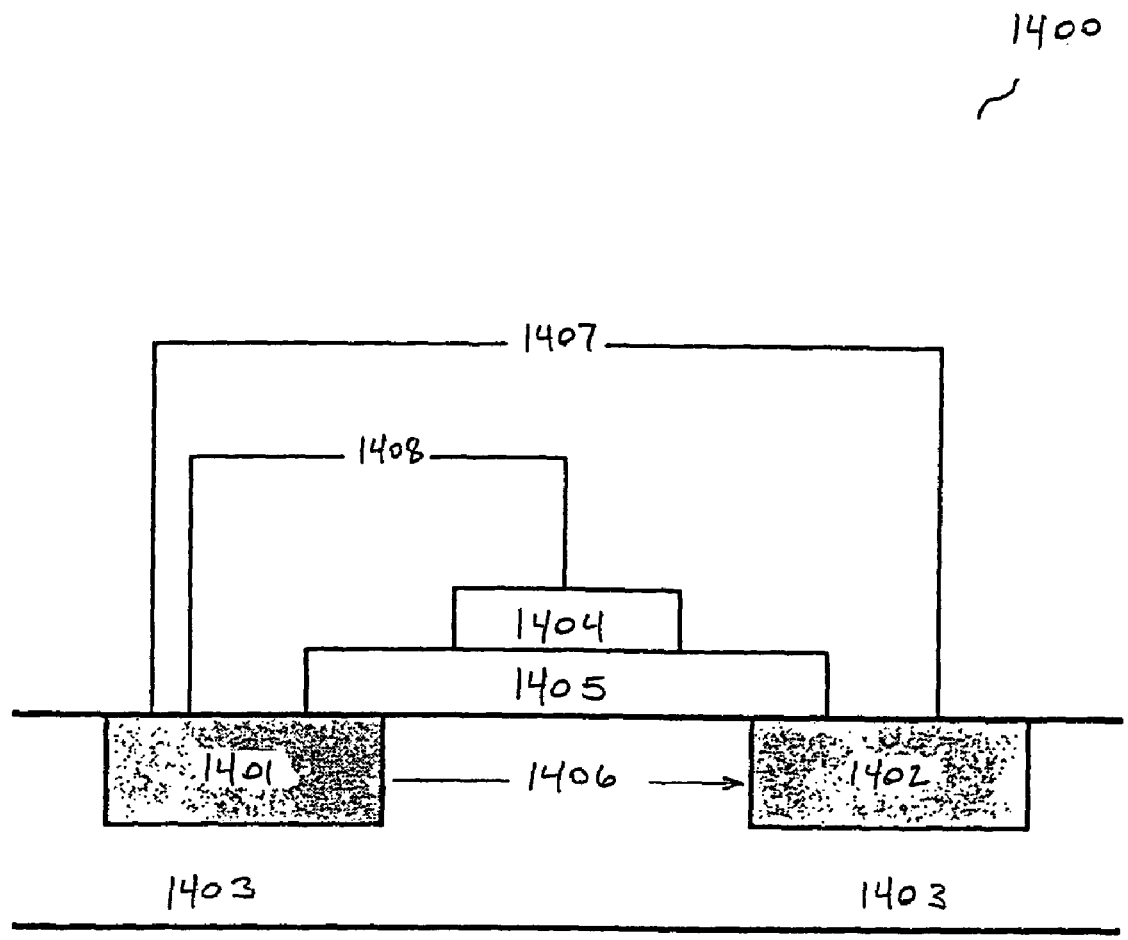
FIG. 14 is a schematic illustration of a field effect transistor fabricated from the n and p-type heterodiamondoid materials of the present invention.

A second type of transistor that may be fabricated from heterodiamondoid-containing materials is shown in FIG. 14. This type of transistor is more often used for data storage in computer memories, and is known as a field effect transistor (FET). Field effect transistors have also been discussed by D. R. Askeland in the above cited reference.

The exemplary heterodiamondoid-containing field effect transistor of FIG. 14, shown generally at 1400, comprises two n-type regions 1401 and 1402 formed in a p-type substrate 1403. The n-type region 1401 is known as the source, and the n-type region 1402 is known as the drain. A third component of the transistor shown generally at 1400 is a conductor, called a gate 1404, which is separated from the p-type substrate 1403 by a thin insulating region of material 1405. The insulator 1405 may comprise a region of undoped diamondoid material; in other words, a diamondoid-based material that is not doped with heteroatoms.

In operation, an electrical potential 1408 is applied between the gate 1404 and the source 1401, where the polarity of the potential in this case is oriented such that the positive side of the voltage 1408 is applied to the gate 1404. The potential draws electrons from the source 1401 toward the vicinity of the gate 1404, but the electrons cannot enter the gate 1404 due to the insulating region 1405 that separates the gate 1404 from the p-type substrate 1403. Electrons are thus concentrated beneath the gate in a region 1406, and this makes the p-type material more conductive in the region 1406 then in the bulk of the p-type substrate shown generally at 1403. The enhanced conductivity of the p-type region 1406 allows a greater number of electrons to flow between the source 1401 and the drain 1402, producing an amplified signal 1407. By changing the input voltage 1408 between the gate 1404 and the source 1401, the number of electrons being conducted through the region 1406 changes, and thus the output voltage 1407 may be controlled as well as amplified.

Examples of p-n junction devices have been discussed in a chapter titled "Semiconductors" by P. Scherz in *Practical Electronics for Inventors* (McGraw-Hill, New York, 2000), pp. 123-190. It is contemplated that these devices may be fabricated from the n and p-type heterodiamondoid materials of the present invention. Basic applications of diodes include half-wave rectifiers, full wave bridge rectifiers, AC to DC power supplies, voltage droppers, voltage regulators, voltage-multiplier circuits, diode clamps, waveform clippers, reverse polarity protectors, transient protectors, and battery-powered backups.

Bipolar transistors may be operated as a transistor switch, a current source, a current biaser, an emitter follower, a common collector amplifier, a common emitter amplifier, and a voltage regulator. Applications of bipolar transistors include relay drivers, differential amplifiers, current mirrors, multiple current sources, multivibrators (flip-flops), and transistor logic gates.

Junction field effect transistors may be operated as light dimmers, basic current sources and amplifiers, source followers, and voltage controlled resistors. The application of a field effect transistor include relay drivers, audio mixers and amplifiers, and electrical field meters.

EXAMPLES

The following examples show methods of synthesizing nitrogen and boron containing heterodiamondoids, and polymerized heterodiamondoids, in accordance with embodiments of the present invention. They are intended to be examples and are not to be viewed as limiting the invention as claimed below.

Examples 1-3 describe methods that could be used to prepare nitrogen containing heterodiamondoids; e.g. azadiamondoids. Example 4 discloses exemplary methods of preparing polymers from heterodiamondoids, including polymers comprising heterodiamondoids coupled through double bonds between diamondoid lattice site carbons. Example 1 demonstrate the preparation of aza tetramantanes from a feedstock which contains a mixture of tetramantanes including some alkyltetramantanes and other impurities. Other feedstocks containing different diamondoids (such as triamantane, or tetramantane and higher diamondoids) may also be applicable and produce similar heterodiamondoid mixtures.

Example 1

Aza Tetramantanes from a Feedstock Containing a Mixture of Tetramantane Isomers

In the following example, a mixture of aza tetramantanes was prepared from a feedstock containing a mixture of the three tetramantane isomers iso-tetramantane, anti-tetramantane, and skew-tetramantane.

A first step in this exemplary synthesis involved the photohydroxylation of a feedstock containing tetramantanes. The feedstock may be obtained by methods described in U.S. patent application Ser. No. 10/052,636, filed Jan. 17, 2002, and incorporated herein by reference in its entirety. A fraction containing at least one of the tetramantane isomers was obtained, and the fraction may have included substituted tetramantanes (such as an alkyltetramantane) and hydrocarbon impurities as well. The gas chromatagraphy/mass spetrometry (GC/MS) of the composition of this fraction showed a mixture of tetramantanes.

A solution of 200 mg of the above feedstock containing tetramantanes in 6.1 g of methylene chloride was mixed with 4.22 g of a solution of 1.03 g (13.5 mmol) of peracetic acid in ethyl acetate. While being stirred vigorously, the solution was irradiated with a 100-watt UV light. Gas evolution was evident from the start. The temperature was maintained at 40-45° C. for an irratiation period of about 21 hours. Then the solution was concentrated to near dryness, treated twice in succession with 10-mL portions of toluene, and reevaporated to dryness. The product was then subjected to GC/MS characterization to show the presence of hydroxylated tetramantane isomers.

In an alternative embodiment, the tetramantane feedstock may be oxidized directly according to the procedures of McKervey et al. (see *J. Chem. Soc., Perkin Trans.* 1, 1972, 2691). The crude product mixture is then subjected to GC/MS characterization to show the presence of iso-tetramantones. The oxidized feedstock as prepared by direct oxidation, wherein the product contains tetramantones, is then reduced with lithium aluminum hydride in ethyl ether at a low temperature. After completion of the reaction, the reaction mixture is worked up by adding saturated $Na_2SO_4$ aqueous solution to decompose excess lithium aluminum hydride at a low temperature. Decantation from the precipitated salts gives a dry ether solution, which, when evaporated, affords a crude product. The crude product may be characterized by GC/MS to show the presence of hydroxylated tetramantane isomers.

In the next step, an azahomo tetramantane-ene may be produced from the above hydroxylated tetramantanes, or from photooxidized tetramantanes. To a stirred and ice cooled mixture of 98% methanesulfonic acid (1.5 ml) and dichloromethane (3.5 ml) was added solid sodium azide (1.52 g, 8.0 mmol). To that mixture was added the hydroxylated tetramantanes as prepared above. To this resulting mixture was added in small increments sodium azide (1.04 g, 16 mmol) over a period of about 0.5 h. Stirring was continued for about 8 h at 20-25° C., and then the mixture was poured into ice water (ca. 10 ml). The aqueous layer was separated, washed with $CH_2Cl_2$ (3 ml), basified with 50% aqueous KOH-ice, and extracted with $CH_2Cl_2$ (10 ml×4). The combined extracts were dried with $Na_2SO_4$, and the solvent was removed to afford a brownish oil product. The product was characterized by GC/MS to show the presence of azahomo tetramantane-ene isomers.

In the next step, an epoxy azahomo tetramantane was made from the azahomo tetramantane-enes via the following procedure. The above mixture was treated with m-CPBA (1.1 equ.) in $CH_2Cl_2$—$NaHCO_3$ at a temperature of about 20° C. for about 12 h, and the reaction mixture was then worked up with a $CH_2Cl_2$ extraction to afford a crude product that was characterized by GC/MS to show the presence of epoxy azahomo tetramantanes.

In the next step, a mixture of N-formyl aza tetramantanes was prepared from the epoxy azahomo tetramantane mixture by irradiating the epoxy aza tetramantane mixture in cyclohexane using a high intensity Hg lamp for about 0.5 hours. The reaction was carried out in an argon atmosphere. Generally speaking, a simpler reaction product was obtained if the reaction was allowed to proceed for only a short time; longer periods gave a complex mixture. The initial product was characterized by GC/MS as a mixture of N-formyl aza tetramantanes.

In a final step, aza tetramantanes was prepared from the above described N-formyl aza tetramantanes by mixing the N-formyl aza tetramantanes with 10 mL of 15% hydrochloric acid. The resultant mixture was heated to a boil for about 24 hours. After cooling, the mixture was subjected to a typical workup to afford a product which was characterized by GC/MS showing the presence of aza tetramantanes.

Example 2

Preparation of Aza Iso-tetramantane from Iso-tetramantane

In this example, an aza iso-tetramantane is prepared from a single tetramantane isomer, iso-tetramantane, as shown in FIGS. 5A-B. As with the mixture of tetramantanes, this synthetic pathway also begins with the photo-hydroxylation of iso-tetramantane or chemical oxidation/reduction to the hydroxylated compound 2a shown in FIG. 5A.

A solution of 3.7 mmol iso-tetramantane in 6.1 g of methylene chloride is mixed with 4.22 g of a solution of 1.03 g (13.5 mmol) of peracetic acid in ethyl acetate. While stirring vigorously, the solution is irradiated by a 100-watt UV light, and gas evolution is evident as soon as the irridation process is started. The temperature is maintained at 40-45° C. for an irradiation period of about 21-hours. The solution is then concentrated to near dryness, treated twice in succession with 10-mL portions of toluene, and reevaporated to dryness. The crude product containing a mixture of iso-tetramantanes hydroxylated at the C-2 and C-3 positions is not purified; instead, the mixture is used directly in a reaction comprising the oxidation of the hydroxylated compound 2a to a keto compound 1.

The photo-hydroxylated iso-tetramantane containing a mixture of C-2 and C-3 hydroxylated iso-tetramantanes is partially dissolved in acetone. The oxygenated components go into solution, but not all of the unreacted iso-tetramantane is capable of being dissolved. A solution of chromic acid and sulfuric acid is then added dropwise until an excess of the acid is present, and the reaction mixture is stirred overnight. The acetone solution is decanted from the precipitated chromic sulfate and unreacted iso-tetramantane, and dried with sodium sulfate. The unreacted iso-tetramantane is recovered by dissolving the chromium salts in water with subsequent filtering. Evaporation of the acetone solution affords a white solid. The crude solid is chromatographed on alumina using conventional procedures, where it may be eluted initially with 1:1 (v/v) benzene/light petroleum ether followed by either ethyl ether or by a mixture of ethyl ether and methanol (95:5 v/v), in order to collect first the unreacted iso-tetramantane and then the keto compound 1. Further purification by recrystallization from cyclohexane may afford a substantially pure product 1.

Alternatively, iso-tetramantane may be directly oxidized to the keto compound 1 according to the procedures of McKervey et al. (*J. Chem. Soc., Perkin Trans.* 1, 1972, 2691). Following the oxidation step, the ketone compound 1 may be reduced to a C-2 hydroxylated iso-tetramantane 2a by treating the ketone compound 1 with excess lithium aluminum hydride in ethyl ether at low temperatures. After completion of the reaction, the reaction mixture is worked up by adding at a low temperature a saturated $Na_2SO_4$ aqueous solution to decompose the excess hydride. Decantation from the precipitated salts gives a dry ether solution, which, when evaporated, affords a crude monohydroxylated iso-tetramantane substituted at the secondary carbon. This compound may be described as a C-2 tetramantan-ol. Further recrystallization from cyclohexane gives a substantially pure product.

Alternatively, a C-2 methyl hydroxyl iso-tetramantane 2b may be prepared from the keto compound 1 by adding dropwise to a stirred solution of keto compound 1 (2 mmol) in dry THF (20 mL) at −78° C. (dry ice/methanol) a 0.8 molar solution (2.8 mL, 2.24 mmol) of methyllithium in ether. The stirring is continued for about 2 hours at −78° C., and for another 1 hour at room temperature. Then, saturated ammonium chloride solution (1 mL) is added, and the mixture extracted with ether (2×30 mL). The organic layer is dried with sodium sulfate and concentrated to give the product 2b, which is subsequently purified by either chromatography or recrystallization.

In the next step, the azahomo iso-tetramantane-ene 3 is prepared from the hydroxylated compound 2. To a stirred and ice-cooled mixture of 98% methanesulfonic acid (15 mL) and dichloromethane (10 mL) is added solid sodium azide (1.52 g, 8.0 mmol), and then either the above C-2 hydroxylated compound 2a or 2b (6 mmol). To the resulting mixture is added in small increments sodium azide (1.04 g, 16 mmol) during a 0.5 hour period. After addition of the sodium azide the stirring is continued for about 8 hours at about 20 to 25° C. The mixture is is then poured onto ice water (ca. 10 mL). The aqueous layer is separated, washed with $CH_2Cl_2$ (3 mL), basified with 50% aqueous KOH-ice, and extracted with $CH_2Cl_2$ (10 mL×4). The combined extracts are dried ($Na_2SO_4$), and the solvent is removed to afford a brownish oil, which is subjected to chromatography purification to afford a substantially pure sample 3 (3a or 3b).

In the next step, an epoxy azahomo iso-tetramantane 4 is prepared from azahomo iso-tetramantane-ene 3. A mixture of the azahomo iso-tetramantane-ene 3 (3a or 3b) with m-CPBA (1.1 equ.) in $CH_2Cl_2$—$NaHCO_3$ is stored at 5-20° C., followed by the usual workup and short column chromatography gives the epoxy azahomo iso-tetramantane 4 (4a or 4b).

In the next step, N-acyl aza iso-tetramantane 5b is prepared from the epoxy azahomo iso-tetramantane 4b by irradiating the epoxy azahomo iso-tetramantane 4b in cyclohexane for about 0.5 hours with a UV lamp. The radiation passes through a quartz filter and the reaction is carried out under an argon atmosphere. Generally speaking, a single product is formed when the reaction is allowed to proceed for only a short time: longer periods gives a complex mixture of products. Products may be isolated by chromatographic techniques.

N-formyl aza iso-tetramantane 5a can be similarly prepared from the epoxy azahomo iso-tetramantane 4a.

In the next step, the aza iso-tetramantane 6 is prepared from N-acyl aza-isotetramantane 5b by heating the N-acyl aza iso-tetramantane 5b (5 mmol) to reflux for about 5 hours with a solution of 2 g powdered sodium hydroxide in 20 mL diethylene glycol. After cooling, the mixture is poured into 50 mL water and extracted with ethyl ether. The ether extract is dried with potassium hydroxide. The ether is distilled off to afford the product aza iso-tetramantane 6. The hydrochloride salt is generally prepared for analysis. Thus, dry hydrogen chloride is passed into the ether solution of the amine, whereby the salt separates out as a crystalline compound. The salt may be purified by dissolving it in ethanol, and precipitating with absolute ether. Typically, the solution is left undisturbed for several days to obtain complete crystallization.

Alternatively, the aza iso-tetramantane 6 may be prepared from the N-formyl aza iso-tetramantane 5a by mixing the N-formyl aza iso-tetramantane 5a (2.3 mmol) with 10 mL of 15% hydrochloric acid. The resultant mixture is heated to a boil for about 24 hours. After mixture is then cooled, and the precipitate filtered and recrystallized from isopropanol to afford the product aza iso-tetramantane 6.

Example 3

Preparation of the Aza Iso-tetramantane 6 Product by Fragmentation of a Keto Compound 1 to an Unsaturated Carboxylic Acid 7

An alternative synthetic pathway for the preparation of the product aza iso-tetramantane 6 is shown in FIG. 5B. Referring to FIG. 5B, the iso-tetramantone 1 as prepared above may be fragmented to the unsaturated carboxylic acid 7 by an abnormal Schmidt reaction per McKervey et al. (*Synth. Commun.*, 1973, 3, 435). It is contemplated that this synthesis is analogous to that reported in the literature for adamantane and diamantane (see, for example, Sasaki et al., *J. Org. Chem.*, 1970, 35, 4109; and Fort, Jr. et al., *J. Org. Chem.*, 1981, 46(7), 1388).

In the next step, the compound 8 may be prepared from the carboxylic acid 7. To 4.6 mmol of the carboxylic acid 7 is added 12 mL of glacial acetic acid and 3.67 g (4.48 mmol) of anhydrous sodium acetate. The mixture is stirred and heated to about 70° C. Lead(IV) acetate (3.0 g, 6.0 mmol, 90% pure, 4% acetic acid) is added in three portions over 30 min. Stirring is continued for 45 min at 70° C. The mixture is then cooled to room temperature and diluted with 20 mL of water. The resulting suspension is stirred with 20 mL of ether, and a few drops of hydrazine hydrate are added to the dissolve the precipitated lead dioxide. The ether layer is then separated, washed several times with water, washed once with saturated sodium bicarbonate, and dried over anhydrous sodium sulfate. Removal of the ether gives an oily material from which a mixture of the two isomers (exo- and endo-) of compound 8 is obtained. Further purification and separation of the stereochemical isomers (exo- and endo-) can be achieved by distillation under vacuum.

Compound 9 (exo- or endo-) may then be prepared from compound 8 (exo- or endo-) by adding to a solution of compound 8 (0.862 mmol) in 5 mL of anhydrous ether 0.13 g (3.4 mmol) of lithium aluminum hydride. The mixture is refluxed with stirring for about 24 hours. Excess lithium aluminum hydride is destroyed by the dropwise addition of water, and the precipitated lithium and aluminum hydroxides are dissolved in excess 10% hydrochloric acid. The ether layer is separated, washed with water, dried over anhydrous sodium sulfate, and evaporated to give compound 9 (which will be a mixture of exo-9 and endo-9 isomers if the starting material was a mixture of exo-8 and endo-8). Further purification may be achieved by recrystallization of the product from methanol-water.

Compound 10 is then prepared from an exo- and endo-mixture of compound 9. A solution of a mixture of the alcohols 9 (1.05 mmol) in 5 mL of acetone is stirred in an Erlenmeyer flask at 25° C. To this solution is added dropwise 8 N chromic acid until the orange color persists; the temperature is maintained at 25° C. The orange solution is then stirred at 25° C. for an addition period of about 3 hours. Most of the acetone is removed, and 5 mL of water is added to the residue. The aqueous mixture is extracted twice with ether, and the combined extracts are washed with saturated sodium bicarbonate, dried over anhydrous sodium sulfate, and evaporated to give crude compound 10. Sublimation on a steam bath gives substantially pure 10.

In an alternative embodiment, the compound 10 may be prepared from an individual isomer of the compound 9, as opposed to the mixture of exo- and endo-9 isomers. For example, compound 10 may be prepared from exo-9 by stirring a solution of exo-9 (1.05 mmol) in 5 mL of acetone in an Erlenmeyer flask at 25° C. To this solution is added dropwise 8 N chromic acid until the orange color persists, the temperature being maintained at about 25° C. The orange solution is then stirred at 25° C. for about 3 hours. Most of the acetone is removed, and 5 mL of water is added to the residue. The aqueous mixture is extracted twice with ether, and the combined extracts are washed with saturated sodium bicarbonate, dried over anhydrous sodium sulfate, and evaporated to give crude 10. Sublimation on a steam bath gives substantially pure 10.

In another alternative embodiment, compound 10 may be prepared directly from the carboxylic acid 7, rather than through intermediate compounds 8 and 9. To this end, a solution of the carboxylic acid 7 (4.59 mmol) in 15 mL of dry THF is stirred under dry argon and cooled to 0° C. A solution of 1.5 g (13.76 mmol) of lithium diisopropylamide in 25 mL of dry THF under argon is added through a syringe to the solution of 7 at such a rate that the temperature does not rise above about 10° C. The resulting solution of the dianion of 7 is stirred at 0° C. for about 3 hours. It is then cooled to about −78° C. with a dry ice-acetone bath, and dry oxygen is bubbled slowly through the solution for about 3 hours or more. A mixture of about 10 mL of THF and 1 mL water is added to the reaction mixture, which is then allowed to warm to room temperature and is stirred overnight. The solution is concentrated to about 10 mL under vacuum, poured into excess 10% HCl, and extracted with ether. The ether layer is washed with 5% NaOH to remove unreacted 7, which may be recovered by acidification of the basic wash. The ether layer is dried over anhydrous sulfate and stripped to yield crude 10. Sublimation on a steam bath at 3-5 torr gives substantially pure product.

Referring again to FIG. 5B, compound 11 may be prepared from compound 10 in the following manner. To a solution of compound 10 (1.6 mmol) in a mixture of pyridine and 95% ethanol (1:1) is added 250 mg (3.6 mmol) of hydroxylamine hydrochloride, and the mixture is stirred at reflux for about 3 days. Most of the solvent is evaporated in a stream of air, and the residue is taken up in 25 mL of water. An ether extract of the aqueous solution is washed with 10% HCl to extract the oxime 11. Neutralization of the acid wash with 10% sodium hydroxide precipitate the oxime 11, which is filtered off and recrystallized from ethanol-water.

In a final step, the aza iso-tetramantane 6 is prepared from compound 11 by the dropwise addition of a solution of compound 11 (0.98 mmol) in 25 mL of anhydrous ether to a stirred suspension of 250 mg (6.58 mmol) of lithium aluminum hydride in 25 mL of anhydrous ether. The mixture is stirred at reflux for about 2 days. Excess lithium aluminum hydride is destroyed with water, and the precipitated lithium and aluminum hydroxides are dissolved in excess 25% sodium hydroxide. The resulting basic solution is extracted twice with ether, and the combined extracts are then washed with 10% HCl. Neutralization of the acidic wash with 10% sodium hydroxide precipitates product 6, which is extracted back into fresh ether. The ether solution is dried over anhydrous sodium sulfate and stripped. The crude product is purified by repeated sublimation on a steam bath under vacuum.

Example 4

Preparation of Polymeric Heterodimondoids Coupled by Double Bonds Between Carbons on Diamond Lattice Positions This example describes an exemplary method that may be used to prepare polymeric heterodimondoids coupled by double bonds between carbon atoms positioned on diamond lattice positions of adjacent heterodiamondoids. In this example, many different configuration of polymeric heterodiamondoids may be prepared, including cyclic, linear, and zig-zag polmers, depending on the positions of the carbon atoms within the diamondoid itself. It will be understood by those skilled in the art that there may be a substantially unlimited number of configurations that may be prepared using the methodology of the present embodiments, but a specific oxidation reaction will be described next, and the coupling reaction is described in Example 9.

Hetero-diamondoidone (keto-heterodiamondoid) is prepared by adding 10 mmoles of hetero-diamondoid to 100 mL of 96% sulfuric acid. The reaction mixture is then heated for about five hours at about 75° C. with vigorous stirring. Stirring is continued at room temperature for about one additional hour. The black reaction mixture is poured over ice and steam distilled. The steam distillate is extracted with ether, and the combined ether extracts are washed with water and dried over $MgSO_4$. Ether is evaporated to yield a crude product mixture. Chromatography on alumina separates the unreacted hetero diamondoid to yield the ketone fraction (eluting with petroleum or other suitable solvent) and by-product alcohol fraction (eluting with ether or other suitable solvent). The yield of the ketone (mixture of different positional and stereo isomers) is generally about 20%. It will be understood by those skilled in the art that some heteroatoms in the heterodiamondoids may need to be protected before being subjected to the oxidation/coupling reactions described herein.

The by-product alcohols from oxidations with strong oxidizing agents such as $H_2SO_4$ or from direct oxidation products of milder oxidations such as with t-butylhydroperoxide can be converted to ketones by treating with $H_2SO_4$ as follows. The alcohol dissolved in 96% $H_2SO_4$ is stirred vigorously at 75° C. for about 4.5 hours in a loosely stoppered flask with occasional shaking. After about 5 hours the reaction is quenched and worked up as above. The total ketone yields are generally about 30%.

Example 5

Preparation of Ketone Compounds with the Ketone Groups Introduced into Double Bond Coupled Hetero Diamondoids with High Selectivity on Methylene Groups Adjacent to the Double Bonds Linking the Diamondoids To a solution of 1 mmol of the double bond coupled heterodiamondoid in 20 mL of $CH_2Cl_2$ is added 1.05 mmol (140 mg) of NCS. The reaction mixture is stirred for about 1 hour at room temperature, diluted with $CH_2Cl_2$, and washed twice with water. The organic layer is dried over $MgSO_4$ and evaporated. The chlorinated products (mixture of different positional or stereo isomers) are produced. The intermediate chlorides are converted to a mixture of the corresponding alcohols and ketones by heating them to around 100° C. in solution of sodium bicarbonate in DMSO for several hours. The product mixture is partitioned between hexane and water and the hexane layer evaporated to yield the product mixture. Conversion of the remaining alcohols to ketones is accomplished by refluxing with a 0.15 mol solution of PCC while stirring for about 2 hours. The ketones are isolated by adding a large excess of diethyl ether to the cooled mixture and washing all solids with additional ether. The ether solution is passed through a short pad of Florisil and the ether evaporated to yield the ketone products with different positional or stereo isomers which may be separated and used for subsequent coupling reactions.

High selectivity for ketone introduction adjacent to double bonds can also be accomplished by selective bromination as shown following: to a solution of 3 mmol of the double bond coupled heterodiamondoid in 40 mL of $CH_2Cl_2$ is added 6.6 mmol (1.175 g) of N-bromosuccinimide (NBS). The reaction mixture is refluxed and stirred for about 12 hours. The reaction mixture is diluted with $CH_2Cl_2$ and washed twice with water and a saturated $Na_2S_2O_3$ solution. The organic layer is dried over $MgSO_4$ and evaporated. The yield of the brominated products is about 90%. Conversion of this intermediate to ketone products is accomplished using the same procedure above.

Example 6

Preparation of Diketones of Heterodiamondoids

Diketones of heterodiamondoids can be produced by more vigorous oxidation than the above examples (Examples 4 and 5) using strong oxidizing agents such as $H_2SO_4$ or $CrO_3/Ac_2O$ but are preferably produced by a sequence of oxidations. First to monoketones or hydroxyketones followed by further oxidation or rearrangement-oxidation, depending on the intermediates involved. The monoketones are generally treated with a solution of $CrO_3$ in acetic anhydride at near room temperature for about 2 days. The reaction is quenched with dilute aqueous caustic (NaOH), and the product isolated by extraction with diethyl ether. The product diketones are then separated and used for coupling reactions.

Example 7

Preparation of Adjacent Ketones on the Same Heterodiamondoid Face

A particularly useful oxidation procedure to produce adjacent ketones on the same diamondoid face is to selectively oxidize an intermediate ketone with $SeO_2/H_2O_2$ to a lactone, then rearrange the lactone to an hydroxyketone with strong acid and oxidize that hydroxyketone to the desired diketone. For example, a monoketone heterodiamondoid is treated at elevated temperature with a 1.5 molar excess of $SeO_2$ in 30% $H_2O_2$ at around 60° C. for several hours. The mixed lactone products are isolated by dilution of the reaction solution with water, extraction with hexane and removal of the hexane by evaporation. The lactones are hydrolyzed and rearranged by heating with 50% $H_2SO_4$. Again the products are isolated as above and further converted to a mixture of positional diketone isomers which are isolated and used for further coupling reactions.

Example 8

Preparation of Mixed Keto-Heterodiamondoids

In some embodiments it may be desirable to produce polymeric heterodiamondoids linked with double bonds via coupling reactions of heterodiamondoid ketones from mixtures of heterodiamondoids. Thus a composition containing a mixture of heterodiamondoids (heterotetramantanes, heteropentamantanes, and the like) is oxidized to produce a mixture of ketones by treatment with 96% $H_2SO_4$ at about 75° C. for about 10 hours or by treating with $CrO_3/Ac_2O$ at near room temperature for about one day. Isolation of the product ketones is accomplished using the procedures described above and are used to prepare mixed polymeric heterodiamondoids by the coupling reaction as described in the next example.

Example 9

Preparation of Polymeric Heterodiamondoids by Coupling Their Keto Derivatives Polymeric heterodiamondoids can be made by coupling their keto derivatives using several procedures. One very useful procedure is the McMurray coupling reaction as described next. Preparation of the reagent (M) (with Mg, K, or Na reducing agent, with Na being the most preferred reducing agent) may be carried out by weighing in a glovebox 20 mmol $TiCl_3$ into a three-necked flask. Then 60 mL of dry solvent (for example, THF) is added. To the stirred slurry the desired amount (generally about 30 to 100 mmol) of Grignard magnesium is added from a Schlenk-tube under argon. The mixture is refluxed for about 3 hours, at which time all the Mg has reacted and the color of the mixture has changed from violet via blue, green, and brown to black. Instead of Mg, an equivalent amount of K, freshly cut and washed with hexane, can be used. The reduction is then complete after a reflux time of about 12 hours.

To prepare the reagent (M) with the $LiAlH_4$ reducing reagent, the $TiCl_3/THF$ mixture is cooled to about 0° C., and the desired amount (generally 15 to 50 mmol) of $LiAlH_4$ is added in small portions to keep the vigorous reaction ($H_2$ evolution) under control. After the addition, the reaction mixture is stirred at 0° C. for about 0.5 hour. If hydrogenation as a side reaction is to be minimized, the black suspension of (M) is refluxed for an additional hour.

The coupling reaction is carried out as follows: the desired amount of ketone (generally 10 to 20 mmol of ketone groups) is added to the cooled, black suspension of (M). A rapid evolution of $H_2$ is observed particularly with $LiAlH_4$ as the reducing agent. After the addition, the mixture is stirred at room temperature for 6 to 20 hours depending on the particular diamondoid being coupled. During the reaction a gentle stream of argon is maintained. Experiments have shown that the above reaction times are sufficient to obtain complete coupling. The reaction is then quenched by adding 40 mL of 2N hydrochloric acid, and the reaction mixture is extracted three times with 10 mL of CHCl$_3$. The combined organic layers are dried over MgSO$_4$, and the solvent evaporated to yield the polymeric hetero higher diamondoids with yields of about 80%. Purification of the products can be accomplished by column chromatography over Al$_2$O$_3$ eluting with suitable solvent for example petroleum ether and recrystallization from suitable solvent.

Using this procedure, the intermediate ketones can be coupled in high yield to produce dimers. Mixed dimers result if two different keto hetero diamondoids are co-coupled. In addition, higher polymeric products form on coupling of multisubstituted hetero diamondoids such as linear rigid rod polymers are formed which have lower solubility and higher melting points than the corresponding zig-zag polymers.

Under special conditions such as high dilution coupling (keto diamondoid concentrations <0.01 molar), cyclic polymeric hetero higher diamondoids can be formed from the diketones that allow ring closure. Generally tetramers are preferred in these cyclization but cyclic trimers also form in special cases. It will be understood by those skilled in the art that it is possible to produce polymeric heterodiamondoids from different keto-heterodiamondoids, their different positional isomers and stereo isomers under this coupling conditions.

Two dimensional sheet polymers can be formed from heterodiamondoids bearing more than 2 ketone groups. Such precursors can be formed by extended oxidations of the parent hetero diamondoids, or by sequential oxidation/couplings as described in the above examples. Cyclic tetramers are particularly useful as intermediates in the production of two dimensional sheets through additional oxidation/coupling sequences as described in the previous examples.

In addition to polymerization using the McMurray coupling reaction other methods of forming double bonds between hetero diamondoids are useful. Another very useful procedure also uses ketones as an intermediate. This method consists of condensing heterodiamondoid (G) ketones with hydrazine to form azines (G=N—N=G), addition of H$_2$S to this azine to form a bisdiamondoid thiadiazolidine, oxidation of this intermediate to a bisdiamondoid thiadiazine and finally elimination of the N and S heteroatoms to produce the desired coupled product (G=G). This procedure is useful as it allows one to systematically produce mixed coupled diamondoid polymers by sequential reaction of one hetero diamondoid then another with hydrazine to form mixed azines. The removal of byproducts from the coupled hetero diamondoids is also easier.

The following is an example of the coupling of heterodiamondoids via this route. To form the azine, a solution of hydrazine hydrate (98%, 1.30 g, 26 mmol) in 15 mL of tert-butyl alcohol is added dropwise under nitrogen over a period of about 45 minutes to a stirred refluxing solution of a heterodiamondoidone (35 mmol) in 60 mL of tert-butyl alcohol. After the addition is complete, the solution is refluxed for about an additional 12 hours and subsequently allowed to stand at ambient temperature for about 24 hours. The solvent is removed to give an crystalline mass ti which is added 200 mL of water. The aqueous mixture is extracted with ether (4×100 mL). The combined ether extracts are washed with brine, dried (MgSO$_4$), and the azine product recrystallized.

To form the thiadiazolidine, hydrogen sulfide is bubbled through a solution of the above azine (41.1 mmol), and 5 mg of p-toluenesilfonic acid in 300 mL of 1:3 acetone:benzene at ambient temperature. Conversion is complete after about 12 hours. The solvent is evaporated to give >90% of the thiadiazolidine. This material is used in the subsequent step without further purification.

To prepare the thiadiazine, a suspension of CaCO$_3$ (20.7 g, 0.21 mol) in 300 mL of benzene at 0° C. is added in several portions lead tetraacetate (20.7 g, 46.7 mmol). The mixture is stirred for about 20 min. A mixture of the above thiadiazolidine (35.9 mmol) and 300 mL of benzene is added dropwise with stirring over a period of about 1.5 hours. After the addition is complete, the mixture is stirred at ambient temperature for about 8 hours. Upon addition of 400 mL of water, a brown precipitate forms which is removed by filtration. The aqueous layer is separated, saturated with NaCl, and extracted with ether. The organic portions are combined, washed with brine, dried over MgSO$_4$, and concentrated to give the thiadiazine with yields of about 90% as a yellow residue. This material is used in the subsequent step without further purification.

To couple heterodiamondoids, an intimate mixture of thiadiazine (3.32 mmol) and triphenylphosphine (2.04 g, 7.79 mmol) is heated at 125-130° C. for about 12 hours under an atmosphere of nitrogen. Column chromatography of the residue over silica gel with suitable solvent gave about 70% yield of the desired coupling products.

Many modifications of the exemplary embodiments of the invention disclosed above will readily occur to those skilled in the art. Accordingly, the invention is to be construed as including all structure and methods that fall within the scope of the appended claims.

What is claimed is:

1. An n-type diamondoid material comprising a diamondoid and a metal atom to enhance electrical conductivity, wherein the diamondoid comprises an electron-donating heteroatom.

2. The n-type diamondoid material of claim 1, wherein the electron-donating heteroatom is a group V element.

3. The n-type diamondoid material of claim 1, wherein the electron-donating heteroatom is selected from the group consisting of nitrogen, phosphorus, and arsenic.

4. The n-type diamondoid material of claim 1, wherein the material comprises an aza-diamondoid.

5. The n-type diamondoid material of claim 1, wherein the electron-donating heteroatom occupies a substitutional site on the diamond lattice.

6. The n-type diamondoid material of claim 1, wherein the electron-donating heteroatom is sp$^3$-hybridized in the diamond lattice.

7. The n-type diamondoid material of claim 1, wherein the diamondoid is selected from the group consisting of adamantane, diamantane, and triamantane.

8. The n-type diamondoid material of claim 1, wherein the material is a molecular crystal.

9. The n-type diamondoid material of claim 1, wherein the metal is gold.

10. An n-type diamondoid material comprising a diamondoid, wherein the diamondoid comprises an electron-donating heteroatom and is selected from the group consisting of tetramantane, pentamantane, hexamantane, heptamantane, octamantane, nonamantane, decamantane, and undecamantane.

11. A p-type diamondoid material comprising a diamondoid and a metal atom to enhance electrical conductivity, wherein the diamondoid comprises an electron-withdrawing heteroatom.

12. The p-type diamondoid material of claim 11, wherein the electron-withdrawing heteroatom is a group III element.

13. The p-type diamondoid material of claim 11, wherein the electron-withdrawing heteroatom is selected from the group consisting of boron and aluminum.

14. The p-type diamondoid material of claim 11, wherein the material comprises a boro-diamondoid.

15. The p-type diamondoid material of claim 11, wherein the electron withdrawing heteroatom occupies a substitutional site on the diamond lattice.

16. The p-type diamondoid material of claim 11, wherein the electron withdrawing heteroatom is $sp^3$-hybridized in the diamond lattice.

17. The p-type diamondoid material of claim 11, wherein the diamondoid is selected from the group consisting of adamantane, diamantane, and triamantane.

18. The p-type diamondoid material of claim 11, wherein the material is a molecular crystal.

19. The polymerized heterodiamondoid p-type diamondoid material of claim 11, wherein the metal is gold.

20. The A p-type diamondoid material comprising a diamondoid, wherein the diamondoid comprises an electron-withdrawing heteroatom and is selected from the group consisting of tetramantane, pentamantane, hexamantane, heptamantane, octamantane, nonamantane, decamantane, and undecamantane.

21. An electrical p-n junction comprising a p-type diamondoid material and an n-type diamondoid material, wherein the n-type diamondoid material comprises a first diamondoid comprising an electron-donating heteroatom and is selected from the group consisting of tetramantane, pentamantane, hexamantane, heptamantane, octamantane, nonamantane, decamantane, and undecamantane and wherein the p-type diamondoid material comprises a second diamondoid comprising an electron-withdrawing heteroatom and is selected from the group consisting of tetramantane, pentamantane, hexamantane, heptamantane, octamantane, nonamantane, decamantane, and undecamantane.

22. The p-n junction of claim 21, wherein the n-type diamondoid material is aza-heterodiamondoid.

23. The p-n junction of claim 21, wherein the n-type diamondoid material is phospho-heterodiamondoid.

24. The p-n junction of claim 21, wherein the p-type diamondoid material is boro-heterodiamondoid.

25. A diamondoid transistor comprising an n-type diamondoid material and a p-type diamondoid material, wherein the n-type diamondoid material comprises a first diamondoid comprising an electron-donating heteroatom and is selected from the group consisting of tetramantane, pentamantane, hexamantane, heptamantane, octamantane, nonamantane, decamantane, and undecamantane and wherein the p-type diamondoid material comprises a second diamondoid comprising an electron-withdrawing heteroatom and is selected from the group consisting of tetramantane, pentamantane, hexamantane, heptamantane, octamantane, nonamantane, decamantane, and undecamantane.

26. The diamondoid transistor of claim 25, wherein the transistor comprises an n-p-n field effect transistor.

27. The diamondoid transistor of claim 25, wherein the transistor comprises a p-n-p field effect transistor.

28. The diamondoid transistor of claim 25, wherein the n-type diamondoid material is aza-heterodiamondoid.

29. The diamondoid transistor of claim 25, wherein the n-type diamondoid material is phospho-heterodiamondoid.

30. The diamondoid transistor of claim 25, wherein the p-type diamondoid material is boro-heterodiamondoid.

31. The diamondoid transistor of claim 25, further comprising a source, gate, and drain, wherein the source and drain are fabricated from the n-type diamondoid material, and the gate is fabricated from the p-type diamondoid material.

32. The diamondoid transistor of claim 25, further comprising a source, gate, and drain, wherein the source and drain are fabricated from the p-type diamondoid material, and the gate is fabricated from the n-type diamondoid material.

33. A diamondoid transistor comprising electrically conducting regions and electrically insulating regions, wherein:
the electrically conducting regions of the transistor comprise n and p-type diamondoid materials, wherein the n-type diamondoid material comprises a first diamondoid comprising an electron-donating heteroatom and is selected from the group consisting of tetramantane, pentamantane, hexamantane, heptamantane, octamantane, nonamantane, decamantane, and undecamantane and wherein the p-type diamondoid material comprises a second diamondoid comprising an electron-withdrawing heteroatom and is selected from the group consisting of tetramantane, pentamantane, hexamantane, heptamantane, octamantane, nonamantane, decamantane, and undecamantane; and
the electrically insulating regions of the transistor comprise undoped diamondoid materials.

34. The transistor of claim 33, wherein the n-type diamondoid material comprises aza-heterodiamondoid.

35. The transistor of claim 33, wherein the n-type diamondoid material comprises phospho-heterodiamondoid.

36. The transistor of claim 33, wherein the p-type diamondoid material comprises boro-heterodiamondoid.

37. A diamondoid material comprising polymerized diamondoids, wherein each diamondoid comprises at least one electron-donating heteroatom or at least one electron-withdrawing heteroatom and further wherein the diamondoids are selected from the group consisting of diamantane, triamantane, tetramantane, pentamantane, hexamantane, heptamantane, octamantane, nonamantane, decamantane, and undecamantane.

38. A diamondoid material comprising a molecular crystal of diamondoids held together by van der Waals forces, wherein each diamondoid comprises at least one electron-donating heteroatom or at least one electron-withdrawing heteroatom and further wherein the diamondoids are selected from the group consisting of adamantane, diamantane, triamantane, tetramantane, pentamantane, hexamantane, heptamantane, octamantane, nonamantane, decamantane, and undecamantane.

* * * * *